United States Patent
Liu et al.

(10) Patent No.: US 6,953,780 B2
(45) Date of Patent: Oct. 11, 2005

(54) ENDOTHELIN ANTAGONIST

(75) Inventors: Keliang Liu, Beijing (CN); Wensheng Yu, Beijing (CN); Yuanjun Liang, Beijing (CN); Hai Wang, Beijing (CN); Yufen Zhao, Beijing (CN); Zhenkai Ding, Beijing (CN)

(73) Assignee: Institute of Pharmacology and Toxicology Academy of Military Medical Sciences, P.L.A., Beijing (CN)

( * ) Notice: Subject to any disclaimer, the term of this patent is extended or adjusted under 35 U.S.C. 154(b) by 0 days.

(21) Appl. No.: 10/312,012

(22) PCT Filed: Jun. 21, 2001

(86) PCT No.: PCT/CN01/01032

§ 371 (c)(1),
(2), (4) Date: May 29, 2003

(87) PCT Pub. No.: WO02/32933

PCT Pub. Date: Apr. 25, 2002

(65) Prior Publication Data

US 2004/0038906 A1 Feb. 26, 2004

(30) Foreign Application Priority Data

Jun. 21, 2000 (CN) ........................................ 00118666 A

(51) Int. Cl.⁷ ........................ A61K 38/06; C07K 5/083; C07K 5/097

(52) U.S. Cl. .......................................... 514/18; 530/331
(58) Field of Search ............................. 514/18; 530/331

(56) References Cited

U.S. PATENT DOCUMENTS 5,260,276 A 11/1993 Cody et al.
5,691,315 A * 11/1997 Ishikawa et al. .............. 514/18

FOREIGN PATENT DOCUMENTS

EP 0 548 441 6/1993
JP 7-228594 8/1995

OTHER PUBLICATIONS

Itoh et al. A Novel Endothelin ETA Receptor Antagonist, BQ–485 . . . Biochemical And Biophysical Research Communications. Sep. 15, 1993, vol. 195, No. 2, pp. 969–975.*

Spellmeyer et al, *Bioorganic Medicinal Chemistry Letters*, 3(4):519–524 (1993).

* cited by examiner

*Primary Examiner*—Jeffrey Edwin Russel
(74) *Attorney, Agent, or Firm*—Sughrue Mion, PLLC

(57) ABSTRACT

The instant invention relates to some tripeptide derivatives having activity against endothelin a process for preparing them, pharmaceutical composition containing the same and their use in prevention or treatment of some diseases associated with endothelin.

9 Claims, No Drawings

ENDOTHELIN ANTAGONIST

This application is a 371 of PCT/CN01/01032, filed Jun. 21, 2002. The disclosure of which is incorporated herein by reference.

FIELD OF THE INVENTION

The present invention claims a priority of chinese appliation No. 00118666.3 as filed an Jun. 21, 2000 and as published on Jan. 9, 2002 in China. The instant invention relates to some tripeptide derivatives having activity against endothelin a process for preparing them, pharmaceutical composition containing the same and their use in prevention or treatment of some diseases associated with endothelin.

Endothelins(ETs), comprised of ET-1, ET-2 and ET-3, as a kind of very important factor constricting the blood vessels are present in human and other mammals. They are all bicyclic 21-amino-acid peptides. ET-1 is not only expressed in no-blood vessel cells, but also the only ET existed in the endothelial cells. ET-2 and ET-3 are mainly expressed in some organs, such as brain, kidney, adrenal gland and small intestine. ETs bring about their biological effects by binding with the special receptor. Up to now, three subtypes of ET receptor, $ET_A$, $ET_B$ and $ET_C$, have been found. $ET_A$ is distributed in the smooth muscular of the aorta, cardiac atrium, placenta, lung, cerebral vessels, and kidney. $ET_B$ is existed in the glial cells of center nervous system and epithelial cells of choroid plexus. $ET_C$ is mainly present in the endothelial cells. The affinities between each of the three subtype receptors and each of ET-1, ET-2 and ET-3 are various. ETs and their receptors take a pathological active part in the essential hypertension, congestive heart failure, myocardial ischemia, cerebral asphyxiation, shock, acute renal failure, and so on. So endothelin antagonists will be helpful in preventing or treating the cardiovascular diseases.

OBJECT OF THE INVENTION

The aim of this invention is seeking novel endothelin antagonists.

SUMMARY OF THE INVENTION

The inventors have found some new tripeptide derivatives having formula I or stereoisomers thereof showed excellent antagonism to endothelin. So the tripeptide derivatives of formula (I) or their stereoisomers can be useful as medicament in preventing or treating the cardiovascular diseases associated with endothelin. The first aspect of the invention is directed to the tripeptide derivatives of formula I or stereoisomers thereof:

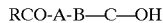

Wherein R is hexamethyleneiminyl- or phenyloxyl-, or RCOA is the group as follows:

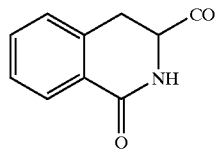

A is Leu, Pro, or other usual aliphatic amino acids, such as β-Ala, γ-aminobutyric acid or aminoisobutyric acid;

B can be D-Trp, D-Pya, D-Phe, wherein the position 2, 3, 4 or 5 of the phenyl in Phe can be substituted by one or two groups selected from halogen, nitro group, carboxyl group or $(C_1-C_4)$-alkyl;

C is D-Trp, D-Pya, D-Phe, wherein the position 2, 3, 4 or 5 of the phenyl in Phe can be substituted by one or two groups selected from halogen, nitro group, carboxyl group or alkyl $C_{1-4}$;

Provided that at least one of B and C is D-Trp.

The another aspect of the invention is directed to a pharmaceutical composition containing the tripeptide derivatives of formula I or their stereoisomers and pharmaceutically acceptable carrier or excipient,

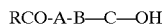

Wherein, R is hexamethyleneiminyl- or phenyl-oxycarbonyl-, or RCOA is the group as follows:

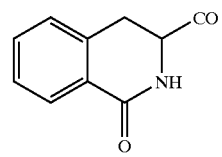

A is Leu, Pro, or other usual aliphatic amino acids, such as β-Ala, γ-aminobutyric acid or aminoisobutyric acid;

B can be D-Trp, D-Pya, D-Phe, wherein the position 2, 3, 4 or 5 of the phenyl in Phe can be one or two substituted by one or two groups selected from halogen, nitro group, carboxyl group or $(C_1-C_4)$-alkyl;

C is D-Trp, D-Pya, D-Phe, wherein the position 2, 3, 4 or 5 of the phenyl in Phe can be substituted by one or two groups selected from halogen, nitro group, carboxyl group or alkyl $C_{1-4}$;

Provided that at least one of B and C is D-Trp.

The invention is also directed to the process for preparing the tripeptide derivatives of formula I or their stereoisomers, which including:

1) reacting RCO-A-OH with B—OP in DMF, DCM, NMM or DIC-HOBt, wherein R, A, B are defined as above, P is $(C_1-C_4)$-alkyl, to form RCO-A-B—OP;

2) saponifying the product of 1) with 1 M NaOH/Methanol and then acidifying with 1 M HCl, to form RCO-A-B—OH;

3) reacting the product of 2) with C—OP in DMF, DCM, NMM or DIC-HOBt, to yield RCO-AAA-B—C—OP, wherein P as defined above, treating the obtained product in a manner same or similar to 2), then forming RCO-A-B—C—OH of formula (I).

The invention is also directed to a use of the tripeptide derivatives of formula I or their stereoisomers in the manufacture of medicament for preventing or treating the diseases or symptoms involving endothelin.

THE DETAILED DESCRIPTION OF THE INVENTION

According to this invention, the term "halogen" includes fluorine, chlorine, bromine, and iodine, and "$(C_1-C_4)$-alkyl" means a straight- or branched-chain saturated alkyl group containing 1 to 4 carbon atoms.

In this invention, the abbreviations represent:

Pro: proline
Leu: leucine
Ala: alanine
Phe: phenylalanine
Trp: tryptophan

Pya: β-pyridinylalanine
GABA: γ-aminobutyric acid
DMF: N,N-dimethylformamide
DCM: dichloromethane
NMM: N-methylmorpholine
DIC-HOBt: N,N'-diisopropylcarbodiimide-1-hydroxyl-benzotriazole
Fmoc: 9-fluorenylmethoxycarbonyl-
HIM: hexamethyleneiminyl- The technical terms "the stereo-isomers of tripeptide derivatives as formula (I)" is directed to the corresponding D- or L-isomers.

More specifically, the invention is also direacted to some new tripeptide derivatives of formula I or their stereoisomers,

RCO-A-B—C—OH     I

Wherein, R is hexamethyleneiminyl- or phenyloxy-, or RCOA is the group as follows:

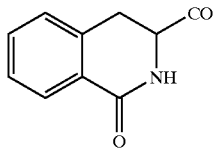

A is Leu, Pro, or other usual aliphatic amino acids, such as β-Ala, γ-aminobutyric acid or aminoisobutyric acid;
B can be D-Trp, D-Pya, D-Phe, wherein the position 2, 3, 4 or 5 of the phenyl in Phe can be one or two substituted by one or two groups selected from halogen, nitro group, carboxyl group or ($C_1$–$C_4$)-alkyl;
C is D-Trp, D-Pya, D-Phe, wherein the position 2, 3, 4 or 5 of the phenyl in Phe can be substituted by one or two groups selected from halogen, nitro group, carboxyl group or alkyl $C_{1-4}$;
Provided that at least one of B and C is D-Trp.

The invention further relates to a pharmaceutical composition containing at least one tripeptide derivative of formula (I) or their stereoisomers and pharmaceutically acceptable carrier or excipient,

RCO-A-B—C—OH     I

Wherein, R is hexamethyleneiminyl- or phenyl-oxy-carbonyl-, or RCOA is the group as follows:

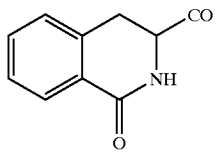

A is Leu, Pro, or other usual aliphatic amino acids, such as β-Ala, γ-aminobutyric acid or aminoisobutyric acid;
B can be D-Trp, D-Pya, D-Phe, wherein the position 2, 3, 4 or 5 of the phenyl in Phe can be one or two substituted by one or two groups selected from halogen, nitro group, carboxyl group or ($C_1$–$C_4$)-alkyl;
C is D-Trp, D-Pya, D-Phe, wherein the position 2, 3, 4 or 5 of the phenyl in Phe can be substituted by one or two groups selected from halogen, nitro group, carboxyl group or alkyl $C_{1-4}$;
Provided that at least one of B and C is D-Trp.

According to this invention, the tripeptide derivatives of formula (I) or their stereoisomers can be selected from the tripeptides as follows:

1 HIM-CO—NH—$CH_2$—$CH_2$—CO-D-Trp-D-Trp-OH
2 HIM-CO-GABA-D-Trp-D-Trp-OH
3 HIM-CO—NH—$(CH_3)_2$—CO-D-Trp-D-Trp-OH
4 HIM-CO-Leu-D-Trp-D-Phe(2-F)—OH
5 HIM-CO-Leu-D-Trp-D-Phe(3-F)—OH
6 HIM-CO-Leu-D-Trp-D-Phe(4-F)—OH
7 HIM-CO-Leu-D-Trp-D-Phe(2-Cl)—OH
8 HIM-CO-Leu-D-Trp-D-Phe(3-Cl)—OH
9 HIM-CO-Leu-D-Trp-D-Phe(4-Cl)—OH
10 HIM-CO-Leu-D-Trp-D-Phe(4-Br)—OH
11 HIM-CO-Leu-D-Trp-D-Phe(3-$NO_2$)—OH
12 HIM-CO-Leu-D-Trp-D-Phe(3-COOH)—OH
13 HIM-CO-Leu-D-Trp-D-Phe(4-COOH)—OH
14 HIM-CO-Leu-D-Trp-D-Phe(3-Cl-4-F)—OH
15 HIM-CO-Leu-D-Trp-D-Phe(2,4-Cl)—OH
16 HIM-CO-Leu-D-Trp-D-Phe(2,5-Cl)—OH
17 HIM-CO-Leu-D-Trp-D-Phe(2-$CH_3$-3-Cl)—OH
18 HIM-CO-Leu-D-Phe(2-F)-D-Trp-OH
19 HIM-CO-Leu-D-Phe(3-F)-D-Trp-OH
20 HIM-CO-Leu-D-Phe(4-F)-D-Trp-OH
21 HIM-CO-Leu-D-Phe(4-Br)-D-Trp-OH
22 HIM-CO-Leu-D-Phe(3-$NO_2$)-D-Trp-OH
23 HIM-CO-Leu-D-Phe(4-F-3-Cl)-D-Trp-OH
24 HIM-CO-Leu-D-Phe(3-CO-D-Trp-OH)-D-Trp-OH
25 HIM-CO-Leu-D-Phe(4-CO-D-Trp-OH)-D-Trp-OH
26 HIM-CO-Leu-D-Phe(2-$CH_3$-3-Cl)-D-Trp-OH
27 Phenoxy-CO-Pro-D-Trp-D-Phe(2-F)—OH
28 Phenoxy-CO-Pro-D-Trp-D-Phe(3-F)—OH
29 Phenoxy-CO-Pro-D-Trp-D-Phe(4-F)—OH
30 Phenoxy-CO-Pro-D-Trp-D-Phe(2-Cl)—OH
31 Phenoxy-CO-Pro-D-Trp-D-Phe(3-Cl)—OH
32 Phenoxy-CO-Pro-D-Trp-D-Phe(4-Cl)—OH
33 Phenoxy-CO-Pro-D-Trp-D-Phe(4-Br)—OH
34 Phenoxy-CO-Pro-D-Trp-D-Phe(3-$NO_2$)—OH
35 Phenoxy-CO-Pro-D-Trp-D-Phe(4-F-3-Cl)—OH
36 Phenoxy-CO-Pro-D-Trp-D-Phe(2,4-Cl)—OH
37 Phenoxy-CO-Pro-D-Trp-D-Phe(2,5-Cl)—OH
38 Phenoxy-CO-Pro-D-Trp-D-Phe(3-COOH)—OH
39 Phenoxy-CO-Pro-D-Trp-D-Phe(4-COOH)—OH
40 Phenoxy-CO-Pro-D-Trp-D-Phe(2-$CH_3$-3-Cl)—OH
o-CPh:

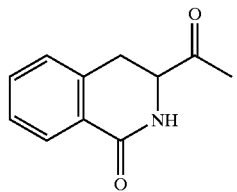

41 o-CPh-D-Trp-D-Phe(2-F)—OH
42 o-CPh-D-Trp-D-Phe(3-F)—OH
43 o-CPh-D-Trp-D-Phe(4-F)—OH
44 o-CPh-D-Trp-D-Phe(2-Cl)—OH
45 o-CPh-D-Trp-D-Phe(3-Cl)—OH
46 o-CPh-D-Trp-D-Phe(4-Cl)—OH
47 o-CPh-D-Trp-D-Phe(4-Br)—OH
48 o-CPh-D-Trp-D-Phe(3-$NO_2$)—OH
49 o-CPh-D-Trp-D-Phe(3-COOH)—OH
50 o-CPh-D-Trp-D-Phe(4-COOH)—OH
51 o-CPh-D-Trp-D-Phe(2,4-Cl)—OH
52 o-CPh-D-Trp-D-Phe(2,5-Cl)—OH
53 o-CPh-D-Trp-D-Phe(2-$CH_3$—Cl)—OH

According to this invention, the tripeptide derivatives of formula (I) or their stereoisomers can be preferably selected from the tripeptides as follows:

1 HIM-CO—NH—CH$_2$—CH$_2$—CO-D-Trp-D-Trp-OH
2 HIM-CO-GABA-D-Trp-D-Trp-OH
3 HIM-CO—NH—(CH$_3$)$_2$—CO-D-Trp-D-Trp-OH
4 HIM-CO-Leu-D-Trp-D-Phe(2-F)—OH
5 HIM-CO-Leu-D-Trp-D-Phe(3-F)—OH
6 HIM-CO-Leu-D-Trp-D-Phe(4-F)—OH
7 HIM-CO-Leu-D-Trp-D-Phe(2-Cl)—OH
8 HIM-CO-Leu-D-Trp-D-Phe(3-Cl)—OH
9 HIM-CO-Leu-D-Trp-D-Phe(4-Cl)—OH
10 HIM-CO-Leu-D-Trp-D-Phe(4-Br)—OH
11 HIM-CO-Leu-D-Trp-D-Phe(3-NO$_2$)—OH
12 HIM-CO-Leu-D-Trp-D-Phe(3-COOH)—OH
13 HIM-CO-Leu-D-Trp-D-Phe(4-COOH)—OH
14 HIM-CO-Leu-D-Trp-D-Phe(3-Cl-4-F)—OH
15 HIM-CO-Leu-D-Trp-D-Phe(2,4-Cl)—OH
16 HIM-CO-Leu-D-Trp-D-Phe(2,5-Cl)—OH
17 HIM-CO-Leu-D-Trp-D-Phe(2-CH$_3$-3-Cl)—OH
18 HIM-CO-Leu-D-Phe(2-F)-D-Trp-OH
19 HIM-CO-Leu-D-Phe(3-F)-D-Trp-OH
20 HIM-CO-Leu-D-Phe(4-F)-D-Trp-OH
21 HIM-CO-Leu-D-Phe(4-Br)-D-Trp-OH
22 HIM-CO-Leu-D-Phe(3-NO$_2$)-D-Trp-OH
23 HIM-CO-Leu-D-Phe(4-F-3-Cl)-D-Trp-OH
24 HIM-CO-Leu-D-Phe(3-CO-D-Trp-O H)-D-Trp-OH
25 HIM-CO-Leu-D-Phe(4-CO-D-Trp-OH)-D-Trp-OH
26 HIM-CO-Leu-D-Phe(2-CH$_3$-3-Cl)-D-Trp-OH

According to this invention, the tripeptide derivatives as formula (I) or their stereoisomers can be prepared by the known methods in the art or the reaction routine as scheme 1:

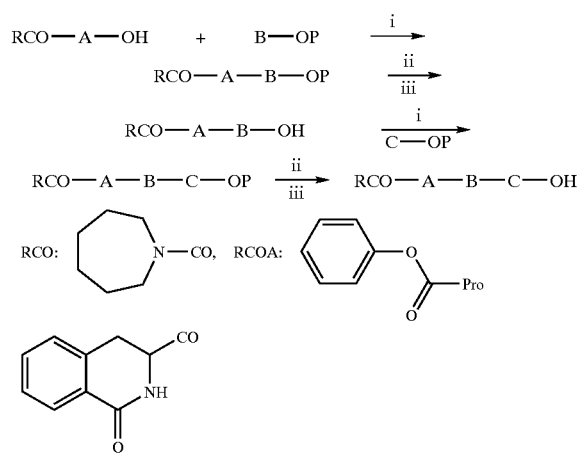

i. DMF, DCM, NNMM, DIC—HOBT;
ii. 1 M NaOH, CH3OH;
iii. 1 M HCl

In the scheme, RCO-A-OH (wherein R and A as defined above) and B—OP (wherein B as defined above, P can be (C$_1$–C$_4$)-alkyl, for example, methyl, ethyl, propyl, isopropyl, butyl, sec-butyl, isoutyl and tert-butyl, preferably methyl and ethyl) are reacted in DMF, DCM, NMM, DIC-HOBt, which yield RCO-A-B—OP (wherein R, A, B and P as defined above). The product RCO-A-B—OP is saponified with 1 M NaOH/Methanol and then acidified with 1M HCl, which yield RCO-A-B—OH (wherein R, A and B as defined above). The product RCO-A-B—OH and C—OP (wherein C and P as defined above) are reacted in DMF, DCM, NMM, DIC-HOBt, which yield RCO-A-B—C—OP (wherein R, A, B, C and P as defined above). The product is saponfied with 1 M NaOH/Methoanol and then acidified with 1 M HCl, then formula I (RCO-A-B—C—OH) or its stereoisomer is produced.

According to this invention, the tripeptide stereoisomers of formula I include D- and/or L-isomers.

According to this invention, the tripeptide derivatives of formula (I) and their stereoisomers exhibit good effect on the test model of ET-1, so can be useful as medicament for animal, especially for human being.

Accordingly, this invention further relates to a pharmaceutical composition containing at least one of the tripeptides of formula I and/or their stereoisomers and pharmaceutically acceptable cerrier or excipient. In general, the of this invention can contain 0.1–90% weight of compound of formula I and/or its stereoisomer. The pharmaceutical composition can be prepared by the known methods. In aim to this, if necessary, the tripeptides of formula (I) and/or their stereoisomers can mix with solid or liquid form of pharmaceutically acceptable excipient or adjuvant to be formulated into a suitable preparation or dosage form for human.

In the present invention, the tripeptide derivatives of formula (I) or pharmaceutical composition containing the same can be administered as a single dosage through intestinal tract or parenteral, such as intramuscular, subcutaneous, nasal, oral mucosa, skin, peritonei or rectum. The preparation can be tablet, capsule, drop pill, aerosol, pill, powder, solution, suspension, emulsion, granule, liposome, trans-skin-membrane system, sublingual tablet, suppository, lyophisized powder for injection and the like. And it can be common preparation, sustained preparation, control releasing preparation, and other microsphere systems.

In order to forming tablet containing a single dosage, most of known carriers can be utilized.

The carriers can be selected from the diluent and absorbent (such as starch, dextrin, gypsum, lactose, mannitol, sucrose, sodium chloride, glucose, carmol, calcium carbonate, kaolin, microcrystaline cellulose, aluminium silicate and the like). The wetting agents and adhesives (such as water, glycerol, polyethylene glycol, ethanol, propanol, starch, dextrin, syrup, honey, glucose solution, acacia slurry, gelatin slurry, sodium carboxymethylcellulos, tachardiacerinic acid, methylcellulose, potassium phosphate, polyvinylpyrrolidone and like it) also can be used. In the preparation, disintegrants can be selected from drying starch, salt of alginic acid, agar powder, brown algae starch, baking soda and citric acid, calcium carbonate, Tween, sodium dodecylsulfonate, methylcellulose, ethylcellulose and so on. The restrainers of disintegrant can be sucrose, tristearin, cocoa butter, hydrogenation of oil and like it, promoters for absorbence may be quaternary ammonium salt, sodium dodecylsulfate. Lubricants used in the preparation can be selected from talcum, silica, maize starch, stearate, boric acid, valelinum liquidum, polyethylene glycol and so on.

Furthermore, the tablet can be formed to coating tablet, for example, sugar coating tablet, film coating tablet, enteric-coated tablet, bistratal tablet or multilaminar tablet.

In order to forming pill containing a single dosage, most of known carriers can be utilized. The examples of carrier can be as follows:

The diluents and adhesives, can selected from glucose, lactose, starch, cocoa butter, hydrogenation of vegetable oil, polyvinylpyrrolidone, gelucire, kaolin, talcum and like it.

The disintegrants can be selected from agar powder, drying starch, the salt of alginic acid, sodium dodecylsulfonate, methylcellulose, ethylcellulose and so on.

In order to prepare the suppository containing a single dosage, the carriers can be known in this field, such as polyethylene glycols, lecithin, cocoa butter, advanced alcohol, the ester of advanced alcohol, gelatin, semi-synthetic glyceride, and so on.

In order to prepare the capsule containing a single dosage, as the active ingredient, the tripeptides or their stereoisomers of formula (I) can be mixed with the carriers as above to be filled into the hard or soft capsule.

The active ingredient, the tripeptides or their stereoisomers of formula (I) can also be formulated into the microspheres or the aqueous suspensions filled in hard capsules or for injection.

In order to form the preparations for the injection containing the active ingredient, such as solution, emulsions, lyophilized powder for injection or suspensions, all diluents in the field, for example, water, alcohol, polyethylene glycol, 1,3-propanediol, ethoxy-iso-stearyl alcohol, multi-oxy-iso stearyl alcohol, Tween, can be used.

Furthermore, in order to prepare the isotonic solutions, sodium chloride, glucose, glycerol, flux, buffer, pH regulator can be added appropriately into the preparation for injection.

In addition, if necessary, coloring agents, antiseptic, perfume, flavoring, sweeting agents or other materials can be added into the preparation.

The dosage of the tripeptides and their stereo-isomers of formula (I) depends on many factors including the character and the severe degree of the disease to be prevented or treated, sex, age, body weight and individual response of the patient or the animal, the specitic compound to be used, the pathway and the frequency of administration, and so on. The dosage above may be single or a few, for example, 2, 3 or 4 dosage pattern.

The following examples and biological activity experiments further illustrate this invention, but should not be understandable or regarded as any limitation to the invention.

PREPARATION EXAMPLE 1

The Synthesis of D,L-N-3-nitro-phenylalanine and Derivatives thereof 1.1 D,L-3-nitrophenylalanine (1aa)

To a stirred suspension of 100 g (0.725 mol.) of 3-nitroaniline in 500 ml of water and 500 ml of concentrated hydrochloric acid, was added dropwise a solution of 59.0 g (0.908 mol.) of sodium nitrite in 150 ml of water and was maintained below −5° C. After the addition, the reaction mixture was clear and stirring was continued for another 20 minutes. 2.0 g. of urea was added and the mixture was stirred for an additional 10 minutes. After the addition of 48.0 g of sodium acetate, the reaction mixture was a yellow clear solution. To this solution of diazol as obtained, under the room temperature, was added a mixture made up of 110 ml. of acrylic acid, 300 ml of acetone and 26.0 g of hydrated copper chloride in 80 ml of water. The temperature was raised slowly (25–100° C./0.5 hr.) and a great quantity of gas bubbles escaped at 60–70° C. while the color of the solution gradually became brown. Stop heating after the completion of the gas produced. The solution was cooled and the organic layer was separated; the aqueous layer was extracted with chloroform (2×150 ml) and combine the organic layer. The combined organic layer was washed with water (3×105 ml) and concentrated to give a red-brown oil. The concentrated product was dissolved with 500 ml of ammonia water and diluted to a 5000 ml clear solution. Kept cooled in an ice bath, the solution was saturated with sufficient ammonia. Then this solution was transferred to a 10L high-pressure pot and reacted under 60° C., 70° C., 80° C. each for one day and 90° C. for two days. After cooled, the reaction solution was taken out and concentrated to 400 ml under reduced pressure. 500 ml. of ethanol was added and cooled in refrigerator. The resulting white solid was filtered and dried to give the title compounds about 100 g.

1.2 D,L-3-nitrophenylalanine Ethyl Ester Hydrochloride (1bb)

180 ml of thionyl chloride was added dropwise slowly to 600 ml of anhydrous alcohol with stirring while the temperature was maintained below −5° C., with the help of an ice-salt bath. Stirring was continued for another 20 minutes and 100 g. of the crude product (1aa) was added. After stirring for two days under room temperature, the reaction mixture was heated under refluxing conditions for 2 hours and filtered while being hot. The filtrate was evaporated to dryness under reduced pressure and a white solid was given. Concentration was repeated for additional two times with anhydrous alcohol and a pure product (1bb) 52.0 g. (26.1%, calculated according to 3-nitroaniline), m.p.184–186° C., was obtained. FAB-MS m/z 239 (M+1-HCl).

1.3 D,L-N-acetyl-3-nitrophenylalanine Ethyl Ester (1cc)

To 150 ml of dry chloroform, 40.0 g (0.146 mol.) of the product (1bb) was added and stirred to dissolve. 45.0 ml. (0.323 mol.) of triethylamine was added and a white solid (triethylamine chloride) was given. 30 ml (0.322 mol.) of acetic anhydride was added dropwise under room temperature and the reaction produced heat. Stirring was continued for another 1 hour after the completion of the addition. The reaction mixture was concentrated under reduced pressure. 50 ml. of water was added and the acetic acid was removed under vacuum.

Another 100 ml. of water was added and the mixture was cooled. The oil solidified. This crude product was filtered and recrystalized from an ethyl acetate-petroleum ether mixture to give a floccule crystal. The yield of the pure product (1cc) was 40.2 g. (98.5%), m.p. 86–87° C., TLC Rf=0.68 (ethyl acetate: petroleum ether=80:20, 254 nm);

$^{1}$HNMR(CDCl$_3$): δ 1.27 (t, J=7.08 Hz, —OCH$_2$CH$_3$), 2.01 (s, 3H, —COCH$_3$), 3.21 (m, 2H, β-H), 4.20 (q, J=7.08 Hz, 2H, —OCH$_2$CH$_3$), 4.88 (m, 1H, α-H), 6.06 (s, 1H, α-NH), 7.46–8.13 (m, 4H, Ar—H).

IR 3260 (NH), 2976 (CH), 1738 (C=O, COOEt), 1646 (C=O, NHCOCH$_3$), 1560, 1523 (CH, Ar), 809, 738, 689 (m-NO$_2$—Ar).

Anal. Calcd. for C$_{13}$H$_{16}$N$_2$O$_3$ (280.28): C, 55.71; H, 5.75; N, 9.99. Found: C, 55.68; H, 5.67; N, 9.52.

PREPARATION EXAMPLE 2

The Synthesis of 2-fluorophenylalanine and It's Derivatives 2.1 D, L-2-fluorophenylalanine (2aa)

The procedure and the ratio of reactant were the same as that described in the example 1 (1aa). 25 ml (0.256 mol.) of 2-fluoroaniline was used. The reaction in the high-pressure pot was carried out for 7 days at 55° C. and the reaction mixture was concentrated to about 100 ml, acidified to pH 4–5 with concentrated HCl. After stood overnight in refrigerator, the precipitate was filtered and dried to give a crude product (2aa) (about 17 g).

2.2 D,L-2-fluorophenylalanine Ethyl Ester Hydrochloride (2bb)

The procedure the ratio of reactant were the same as the example 1 (1bb). 17.0 g. of the crude product (2aa) was used. The resulting colorless needle crystal was collected to give 16.0 g (2bb). (24.7%, calculated according to 2-fluoroaniline), m.p. 112–115° C., FAB-MS m/z 212 (M+1-HCl).

2.3 D,L-N-acetyl-2-fluorophenylalanine Ethyl Ester (2cc)

The same as the example 1 (1cc). 16.0 g. (0.065 mol.) of (2bb) was used. 100 ml ethyl acetate was added to the concentrate, then washed in order with water, 1 M hydrochloric acid, saturated solution of sodium hydrogen carbonate and saturated solution of sodium chloride. The ethyl acetate layer was dried with anhydrous sodium sulfate, filtered and concentrated. The crude product was recrystallized from an ether-petroleum ether to give a colorless crystal (2cc). The yield was 13.0 g. (79.0%), m.p.58–61° C.

TLC Rf=0.63 (A).

$^1$HNMR(CDCl$_3$): δ 1.22 (t, J=7.12 Hz, —OCH$_2$CH$_3$), 1.96 (s, 3H, —COCH$_3$), 3.14 (m, 2H, β-H), 4.15 (m, 2H, —OCH$_2$CH$_3$), 4.82 (m, 1H, α-H), 5.98 (s, 1H, α-NH), 6.98–7.22 (m, 4H, Ar—H).

IR 3334 (NH), 2964 (CH), 1726 (C=O, COOEt), 1646 (C=O, NHCOCH$_3$), 1553, 1498 (CH, Ar), 753 (o-F—Ar).

Anal. Calcd. for C$_{13}$H$_{16}$NFO$_3$ (253.27): C, 61.65; H, 6.37; N, 5.53. Found: C, 61.65; H, 6.44; N, 5.75.

PREPARATION EXAMPLE 3

The Synthesis of 3-fluorophenylalanine and It's Derivatives 3.1 D,L-3-fluorophenylalanine (3aa)

The method and the ratio of the materials were the same as that described in the synthesis of (1aa). 25 ml. (0.256 mol.) 3-fluoroaniline was used. The reaction in the high-pressure pot was carried out for 8 days at 50° C. and the reaction mixture was concentrated to about 100 ml, acidified to pH 4–5 with concentrated hydrochloric acid. After stood overnight in refrigerator, the precipitate was filtered and dried to give a crude product (3aa) which was about 25 g. FAB-MS m/z 184 (M+1).

3.2 D,L-3-fluorophenylalanine Ethyl Ester Hydrochloride (3bb)

The method was the same as (1bb). 24.0 g. of the crude product (3aa) was used. 10 ml. of anhydrous alcohol and 50 ml. of ether were added to the concentrate of the reaction solution. This stood for a week below 0° C. and the resulting colorless needle crystal was collected to give (3bb) 20.0 g. (31.4%, calculated according to 3-fluoroaniline), m.p. 119–121° C.

3.3 D,L-N-acetyl-3-fluorophenylalanine Ethyl Ester (3cc)

The method was the same as (1cc). 20.0 g. (0.080 mol.) of (2bb) was used. 100 ml. of ethyl acetate was added to the concentrate, then washed in order with water, 1M hydrochloric acid, saturated solution of sodium hydrogen carbonate and saturated solution of sodium chloride. The ethyl acetate layer was dried with anhydrous sodium sulfate, filtered and concentrated. The crude product was recrystallized from an ether-petroleum ether to give a colorless crystal (3cc). The yield was 16.0 g. (78.9%), m.p.75–77° C.

TLC Rf=0.60 (A).

$^1$HNMR(CDCl$_3$): δ 1.25 (t, J=7.32 Hz, —OCH$_2$CH$_3$), 2.00 (s, 3H, —COCH$_3$), 3.12 (m, 2H, β-H), 4.18 (q, J=7.32 Hz, 2H, —OCH$_2$CH$_3$), 4.85 (m, 1H, α-H), 6.00 (s, 1H, α-NH), 6.80–7.27 (m, 4H, Ar—H).

IR 3334 (NH), 2989, 2939 (CH), 1732 (C=O, COOEt), 1646 (C=O, NHCOCH$_3$), 1529 (CH, Ar), 776, 701 (m-F—Ar). Anal. Calcd. for C$_{13}$H$_{16}$NFO$_3$ (253.27): C, 61.65; H, 6.37; N, 5.53. Found: C, 61.70; H, 6.26; N, 5.37.

PREPARATION EXAMPLE 4

The Synthesis of 4-fluorophenylalanine and It's Derivatives 4.1 D,L-4-fluorophenylalanine (4aa)

The method and the ratio of the materials were the same as described in the synthesis of (1aa). 100 ml (1.04 mol.) 4-fluoroaniline was used. The reaction in the high-pressure pot was carried out for 7 months under room temperature and the reaction mixture was concentrated to about 300 ml, acidified to pH 3 with concentrated hydrochloric acid. After stood overnight in refrigerator, the precipitate was filtered and dried to give a crude product (4aa) which was about 150 g.

4.2 D,L-4-fluorophenylalanine Ethyl Ester Hydrochloride (4bb)

The method was the same as (3bb). 150.0 g. of the crude product (4aa) was used and 81.0 g. (31.5%, calculated according to 4-fluoroaniline) of the product (4bb) was collected, m.p. 130–132° C. FAB-MS m/z 212 (M+1-HCl).

4.3 D,L-N-acetyl-4-fluorophenylalanine Ethyl Ester (4cc)

The method was the same as (3cc). 40.0 g (0.162 mol.) of (4bb) was used and 39.0 g. (95.0%) of the product (4cc) was collected, m.p. 71–73° C.

TLC Rf=0.68 (A)

$^1$HNMR(CDCl$_3$): δ 1.25 (t, J=7.02 Hz, —OCH$_2$CH$_3$), 2.00 (s, 3H, —COCH$_3$), 3.10 (m, 2H, β-H), 4.17 (m, 2H, —OCH$_2$CH$_3$), 4.84 (m, 1H, α-H), 6.01 (s, 1H, α-NH), 6.95–7.09 (m, 4H, Ar—H).

IR 3309 (NH), 3087, 2989 (CH), 1756 (C=O, COOEt), 1658 (C=O, NHCOCH$_3$), 1553 (CH, Ar), 830, 800, 707 (p-F—Ar).

Anal. Calcd. for C$_{13}$H$_{16}$NFO$_3$ (253.27): C, 61.65; H, 6.37; N, 5.53. Found: C, 61.56; H, 6.30; N, 5.25.

PREPARATION EXAMPLE 5

The Synthesis of 2-chlorophenylalanine and It's Derivatives 5.1 D,L-2-chlorophenylalanine (5aa)

The method and the ratio of the materials were the same as described in the synthesis of (1aa). 51.5 g (0.40 mol.) of 2-chloroaniline was used. The reaction in the high-pressure pot was carried out for 5 months under room temperature and the reaction mixture was concentrated to about 300 ml, acidified to pH 3 with concentrated hydrochloric acid. This was filtered to give 19.8 g of product. The filtrate was concentrated, stood overnight in refrigerator and 28.0 g of product was collected again. The total yield of the crude product (5aa) was 47.8 g.

5.2 D,L-N-acetyl-2-chlorophenylalanine (5bb)

To solution of 15.6 g (0.078 mol.) of the product (5aa) in 156 ml of 2M sodium hydroxide was added dropwise 15 ml. of acetic anhydride at −5° C. Stirring was continued for additional 10 minutes and 23 ml. of concentrated hydrochloric acid was added to the reaction mixture to make its pH about 3. After stood overnight in refrigerator, the mixture was filtered to give a white solid. The yield was 14.0 g. (74%), m.p. 158–160° C.

5.3 D,L-N-acetyl-2-chlorophenylalanine Ethyl Ester (5cc)

The method was the same as (1bb). 13.3 g. of the product (5bb), 170 ml. of anhydrous alcohol and 8.5 ml. of thionyl chloride were used and the reaction was carried out for 4 hours under room temperature. The reaction solution was concentrated under reduced pressure. The residue was poured in to 500 ml. of water and stood overnight in refrigerator. This was filtered to give 12.0 g. (81%) of product, m.p. 63–65° C.

TLC Rf=0.61 (A)

$^1$HNMR(CDCl$_3$): δ 1.25 (t, J=7.12 Hz, —OCH$_2$CH$_3$), 2.00 (s, 3H, —COCH$_3$), 3.20–3.36 (m, 2H, β-H), 4.14–4.24 (m, 2H, —OCH$_2$CH$_3$), 4.94 (m, 1H, α-H), 6.04 (s, 1H, α-NH), 7.22–7.40 (m, 4H, Ar—H).

FAB-MS m/z 270.2(M)

IR 3334 (NH), 3063, 2976 (CH), 1726 (C=O, COOEt), 1640 (C=O, NHCOCH$_3$), 1547 (CH, Ar), 750 (o-Cl-Ar).

Anal. Calcd. for C$_{13}$H$_{16}$NClO$_3$ (269.71): C, 57.89; H, 5.98; N, 5.19. Found: C, 58.30; H, 5.94; N, 4.80.

PREPARATION EXAMPLE 6

The Synthesis of 3-chlorophenylalanine and It's Derivatives 6.1 D,L-3-chlorophenylalanine (6aa)

The method and the ratio of the materials were the same as that described in the synthesis of (1aa). 96.0 g (0.784 mol.) of 3-chloroaniline was used. The reaction in the high-pressure pot was carried out for 10 days at 60° C. The reaction mixture was concentrated and filtered to give 87 g. of crude product. After washed with ether, the yield was 66 g.

6.2 D,L-3-chlorophenylalanine Ethyl Ester Hydrochloride (6bb)

The method was the same as (1bb). 66 g. (0.33 mol.) of the crude product (6aa), 400 ml. of anhydrous ethanol and 110 ml of thionyl chloride were used. The crude product was recrystallized from an ethanol-ether mixture. The yield of the pure product was 63.0 g. (31.7%, calculated according to 3-chloroaniline), m.p. 138.5–140.5° C., FAB-MS m/z 228.0 (M+1-HCl).

6.3 D,L-N-acetyl-3-chlorophenylalanine Ethyl Ester (6cc)

The method was the same as (1cc). 40.0 g (0.162 mol.) of (6bb) was used and the yield of the product (6cc) was 40.0 g. (98.0%), m.p. 88–90° C.

TLC Rf=0.69 (A).

$^1$HNMR (CDCl$_3$): δ 1.24 (t, J=7.25 Hz, —OCH$_2$CH$_3$), 1.99 (s, 3H, —COCH$_3$), 3.08 (m, 2H, β-H), 4.16 (m, 2H, —OCH$_2$CH$_3$), 4.84 (m, 1H, α-H), 6.06 (s, 1H, α-NH), 6.98–7.26 (m, 4H, Ar—H).

IR 3334 (NH), 2989(CH), 1750 (C=O, COOEt), 1652 (C=O, NHCOCH$_3$), 1547 (Ar—H), 880, 787, 692 (m-Cl—Ar)

Anal Calcd for C$_{13}$H$_{16}$NClO$_3$: 57.89 (C), 5.98 (H), 5.19 (N)

MW 269.17 Found: 57.86 (C), 5.93 (H), 5.08 (N)

PREPARATION EXAMPLE 7

The Synthesis of 4-bromophenylalanine and It's Derivatives 7.1 D,L-Phe(4-Br)OH (7aa)

The procedure and ratio of reactant were same as that in (1aa), 4-Br-aniline 100.0 g (0.58 mol) was aminolysised an half year at room temperature. Concentrated and filtrated. Give the rude product about 81 g. (undissolved in water.) FAB-MS M/Z 245.2 (M+1)

7.2 D,L-Phe(4-Br)OC$_2$H$_5$ HCl (7bb)

Method was the same was same as (1bb). Added the above crude product (7aa) 80 g (0.33 mol), C$_2$H$_5$OH 400 ml, SOCl$_2$150 ml. obtained 61.0 g (34.0%, cal. by 4-Br-aniline) (7bb). m.p. 166–168° C.

7.3 D,L-N-Ac-Phe(4-Br)OC$_2$N$_5$ (7cc)

Method was the same as (1cc). Added (7bb) 40.0 g (0.143 mol), gave (7cc) 42.0 g (94.0%). m.p. 90–92° C.;

TLC/Rf=0.57(A).

$^1$HNMR(CDCl$_3$): δ 1.23 (t, J=7.14H$_2$, —OCH$_2$CH$_3$), 1.97 (S, 3H, —COCH$_3$), 3.04 (m, 2H, β-H), 4.14 (m, 2H, —OCH$_2$CH$_3$), 4.84 (m, 1H, α-H), 5.90 (S, 1H, α-NH), 5.94–7.39 (m, 4H, Ar—H).

IR 3334 (NH), 3001 (CH), 1744 (C=O, COOEt), 1652 (C=O, NHCOCH$_3$), 1535 (CH, Ar—H), 815 (4-Br—Ar)

Anal Calc'd for C$_{13}$H$_{16}$NBrO$_3$: 49.70 (C), 5.13 (H), 4.46 (N) Found: 49.787 (C), 4.99 (H), 4.16 (N)

PREPARATION EXAMPLE 8

The Synthesis of Phe(4-F-3-Cl)OH and It's Derivatives 8.1 D,L-Phe(4-F-3-Cl)OH (8aa)

The procedure and ratio were same as (1aa). 4-F-3-Cl-aniline 80 g (1.00 mol) was aminolysised for ten months at room temperature. Concentrated to 500 ml under reduced pressure, and then acidified to pH 3 with conc. HCl. The crystals that separated were collected and dried, give the crude product (8aa) about 196.0 g. FAB-MS m/z 218(M), 220 (M+2).

8.2 D,L-Phe(4-F-3-Cl)OCH$_2$CH$_3$ HCl (8bb)

Method was the same as (1bb). Added the above crude product (8aa) 196.0 g give 126.0 g (44.4%, cal. by 4-F-3-Br-aniline) (8bb). m.p. 136–138° C.

8.3 D,L-N-Ac-Phe(4-F-3-Cl)OCH$_2$CH$_3$ (8cc)

Method was the same as (1cc). Added (8bb) 41.0 g (0.145 mol), gave (8cc) 39.6 g (94.7%). m.p. 106–107° C.;

TLC/Rf=0.54(A).

$^1$HNMR(CDCl$_3$): δ 1.26 (t, J=7.02H$_2$, —OCH$_2$CH$_3$), 2.02 (S, 3H, —COCH$_3$), 3.10 (m, 2H, β-H), 4.19 (q, J=7.02 Hz, 2H, —OCH$_2$CH$_3$), 4.80 (q, 1H, α-H), 6.01 (S, 1H, α-NH), 6.97–7.16 (m, 3H, Ar—H).

IR 3297 (NH), 3001 (CH), 1750 (C=O, COOEt), 1652 (C=O, NHCOCH$_3$), 1535 (CH, Ar—H), 866, 827, 695 (p-F-m-Cl—Ar)

Anal Calc'd for C$_{13}$H$_{16}$NFClO$_3$: 59.27 (C), 5.25 (H), 4.87 (N) Found: 54.11 (C), 5.15 (H), 4.86 (N)

PREPARATION EXAMPLE 9

The Synthesis of Phe(2,4-di-Cl)OH and It's Derivatives 9.1 D,L-Phe(2,4-di-Cl)OH (9aa)

The procedure and ratio were same as (1aa) 2,5-di-Cl-aniline 80 g (0.50 mol) was aminolysised ten months at room temperature. Concentrated to 500 ml under reduced pressure, and then acidified to PH3 with conc. HCl. The crystals that separated were collected and dried, give the crude product (9aa) about 103.0 g.

9.2 D,L-Phe(2,4-di-Cl)OCH$_2$CH$_3$ HCl (9bb)

Method was the same as (1bb). Added the above crude product (9aa) 100 g give 59.0 g (32.1%, cal. by 2,4-di-Cl-aniline) (9bb). m.p. 136–138° C. FAB-MS m/z 262.0(M), 264 (M+2)

9.3 D,L-N-Ac-Phe(2,4-di-Cl)OCH$_2$CH$_3$ (9cc)

Method was the same as (1cc). Added (9bb) 54.4 g (0.182 mol), gave (9cc) 53.0 g (96.0%). m.p. 109–111° C.;

TLC/Rf=0.66(A).

$^1$HNMR(CDCl$_3$): δ 1.21 (t, J=7.18H$_2$, —OCH$_2$CH$_3$), 1.92 (S, 3H, —COCH$_3$), 3.19 (m, 2H, β-H), 4.13 (q, J=7.02 Hz, 2H, —OCH$_2$CH$_3$), 4.85 (q, 1H, —H), 5.97 (S, 1H, α-NH), 7.11–7.36 (m, 3H, Ar—H).

IR 3322 (NH), 2989 (CH), 1726 (C=O, COOEt), 1646 (C=O, NHCOCH$_3$), 1553 (CH, Ar—H), 867, 849, 818 (p-Cl-o-Cl—Ar)

Anal Calc'd for C$_{13}$H$_{16}$NFClO$_3$: 51.33 (C), 4.97 (H), 4.60 (N) Found: 51.38 (C), 4.92 (H), 4.34 (N)

PREPARATION EXAMPLE 10

The Synthesis of Phe(2,5-di-Cl)OH and It's Derivatives

10.1 D,L-Phe(2,5-di-Cl)OH (10aa)

The procedure and ratio were same as (1aa). 2,4-di-Cl-aniline 80 g (0.50 mol) was aminolysised for ten days at 50° C. Concentrated to 300 ml under reduced pressure, and then acidified to PH3 with conc. HCl. The crystals that separated were collected and dried, give the crude product (10aa) about 25 g.

10.2 D,L-Phe(2,5-di-Cl)OCH$_2$CH$_3$ HCl (10bb)

Method was the same as (1bb). Added the above crude product (10aa) 25 g, give 16 g (8.7%, cal. by 2,5-di-Cl-aniline) (10bb). m.p. 184–188° C. FAB-MS m/z 262.0(M), 264 (M+2)

10.3 D,L-N-Ac-Phe(2,5-di-Cl)OCH$_2$CH$_3$ (10cc)

Method was the same as (1cc). Added (10bb) 20.7 g (0.064 mol), gave (10cc) 19.20 g (91.0%). m.p. 116–118° C.;

TLC/Rf=0.63(A).

$^1$HNMR(CDCl$_3$): δ 1.23 (t, J=7.15H$_2$, —OCH$_2$CH$_3$), 1.98 (S, 3H, —COCH$_3$), 3.22 (m, 2H, β-H), 4.14 (q, J=7.08 Hz, 2H, —OCH$_2$CH$_3$), 4.87 (q, 1H, α-H), 6.01 (S, 1H, α-NH), 7.14–7.36 (m, 3H, Ar—H).

IR 3297 (NH), 3075, 2989 (CH), 1744 (C=O, COOEt), 1658 (C=O, NHCOCH$_3$), 1541 (CH, Ar—H), 815, 713 (2,5-di-Cl-Ar)

Anal Calc'd for C$_{13}$H$_{16}$NCl$_2$O$_3$: 51.33 (C), 4.97 (H), 4.60 (N) Found: 51.38 (C), 4.98 (H), 4.39 (N).

PREPARATION EXAMPLE 11

The Synthesis of Phe(3,4-di-Cl)OH and It's Derivatives

11.1 D,L-Phe(3,4-di-Cl)OH (11aa)

The procedure and ratio were same as (1aa). 3,4-di-Cl-aniline 250 g (1.56 mol) was aminolysised for 7 days at 50° C. concentrated to 1000 ml under reduced pressure, and then acidified to PH3 with conc. HCl. The crystals that separated were collected and dried, gave the crude product (11aa) about 287.0 g.

11.2 D,L-Phe(3,4-di-Cl)OCH$_3$.HCl (11bb)

Method was the same as (1bb). Added the above crude product (11aa) 287.0 g, gave 159.0 g (36.2%, cal. by 3,4-di-Cl-aniline) (11bb). m.p. 127–130° C. FAB/MS m/z 249.0(M), 251(M+2).

11.3 D,L-N-AC-Phe(3,4-di-Cl)OCH$_3$ (11cc)

Method was the same as (1cc). Added (11bb) 11.0 g (0.039 mol), gave (11cc) 8.0 g (71.3%).

m.p.101–103° C.; TLC/R$_f$=0.62(A);

$^1$HNMR(CDCl$_3$): δ 1.20 (t, J=7.12 Hz, —OCH$_2$CH$_3$), 2.09 (s, 3H, —COCH$_3$), 3.15 (m, 2H, β-H), 4.13 (q, J=7.11 Hz, —OCH$_2$CH$_3$), 4.85 (q, 1H, α-H), 5.97 (s, 1H, α-NH), 7.05–7.36 (m, 3H, Ar—H);

IR 3322 (NH), 3075, 2964 (CH), 1732 (C=O, COOEt), 1652 (C=O, NHCOCH$_3$), 1547 (CH, —C$_6$H$_5$), 898, 830 (p and m-C$_6$H$_5$).

PREPARATION EXAMPLE 12

The Synthesis of Phe(2-Cl-4-Br)OH and It's Derivatives

12.1 D,L-Phe(2-Cl-4-Br)OH (12aa)

The procedure and ratio of reactant were same as (1aa). 2-Cl-4-Br-aniline 10 g (0.048 mol) was aminolysised for 5 months at room temperature, concentrated to 100 ml under reduced pressure, and then acidified to PH3 with conc. HCl. The crystals that separated were collected and dried, gave the crude product (12aa) about 5.6 g.

12.2 D,L-Phe(2-Cl-4-Br)OCH$_2$CH$_3$.HCl (12bb)

Method was the same as (1bb). Added the above crude product (12aa) 5.6 g, gave 5.1 g (30.7%, cal. by 2-Cl-4-Br-aniline) (12bb). m.p.172–174° C.

FAB/MS m/z 308.0(M+1).

$^1$HNMR(CDCl$_3$): δ 1.20 (t, J=7.02 Hz, —OCH$_2$CH$_3$), 3.28–3.34, 3.42–3.48 (m, 2H, β-H), 4.21–4.26 (m, 2H, —OCH$_2$CH$_3$), 4.45 (m, 2H, α-NH$_2$), 7.25–7.74 (m, 3H, Ar—H);

IR 3445 (NH$_2$.HCl), 2939 (CH), 1750 (C=O, COOEt), 1590 (CH, —C$_6$H$_5$), 855, 821 (p-Br and o-Cl—C$_6$H$_5$).

Anal. Calcd. For C$_{11}$H$_{14}$NBrCl$_2$O$_2$: C, 38.51; H, 4.11; N, 4.08. Found: C, 38.56; H, 4.18; N, 4.02.

PREPARATION EXAMPLE 13

Synthesis of Phe(2-CH$_3$-3-Cl)OH and It's Derivatives

13.1 D,L-Phe(2-CH$_3$-3-Cl)OH (13aa)

The procedure and ratio of reactant were same as (1aa). 2-CH$_3$-3-Cl-aniline 142 g (1.0 mol) was aminolysised for 5 months at room temperature, concentrated to 100 ml under reduced pressure, and then acidified to PH3 with conc. HCl. The crystals that separated were collected and dried, gave the crude product (13aa) about 105.6 g.

13.2 D,L-Phe(2-CH$_3$-3-Cl) OCH$_2$CH$_3$.HCl (13bb)

Method was same as (1bb). Added the above crude product (13aa) 105.6 g, gave 74.0 g (26.7%, cal. by 2-CH$_3$-3-Cl-aniline) (13bb). m.p. 142–144° C. FAB/MS m/z 242.2 (M–HCl)

13.3 D,L-N-AC-Phe(2-CH$_3$-3-Cl) OCH$_2$CH$_3$ (13cc)

Method was the same as (1cc). Added (13bb) 19.0 g (69 mmol), gave (13cc) 19.0 g (98.1%). m.p.106–107° C.;

TLC/R$_f$=0.73(A);

$^1$HNMR(CDCl$_3$): δ 1.16 (t, J=7.32 Hz, —OCH$_2$CH$_3$), 1.96 (s, 3H, —COCH$_3$), 3.01 (m, 2H, β-H), 4.12 (q, J=7.11 Hz, —OCH$_2$CH$_3$), 4.82 (q, 1H, α-H), 6.08 (s, 1H, α-NH), 7.01–7.27 (m, 3H, Ar—H);

IR 3284 (NH), 3075, 2976, 2939 (CH), 1756 (C=O, COOEt), 1652 (C=O, NHCOCH$_3$), 1560, 1498 (CH, —C$_6$H$_5$), 796, 707 (2-CH$_3$-3-Cl C$_6$H$_5$).

Anal. Calcd. For C$_{14}$H$_{18}$NClO$_3$:C, 59.26; H, 6.39; N, 4.94. Found: C, 59.47; H, 6.42; N, 4.72.

PREPARATION EXAMPLE 14

Synthesis of Phe(2-CH$_3$-4-NO$_2$)OH and It's Derivatives

14.1 D,L-Phe(2-CH$_3$-4-NO$_2$)OH (14aa)

The procedure and ratio of reactant are same as (1aa). 2-CH$_3$-4-NO$_2$-aniline 50 g (0.33 mol) was aminolysised for 5 months at room temperature. concentrated to 100 ml under reduced pressure, and then acidified to PH3 with conc. HCl. The crystals that separated were collected and dried, gave the crude product (14aa) about 32.6 g.

14.2 D,L-Phe(2-CH$_3$-4-NO$_2$)OCH$_2$CH$_3$.HCl (14bb)

Method was the same as (1bb). Added the above crude product (14aa) 32.6 g, gave 26.0 g (27.4%, cal. by 2-CH$_3$-4-NO$_2$-aniline) (14bb). m.p. 172–175° C. FAB/MS m/z 253.0 (M+1-HCl)

14.3 D,L-N-AC-Phe(2-CH$_3$-4-NO$_2$) OCH$_2$CH$_3$ (14cc)

Method was the same as (1cc). Added (14bb) 19.0 g (66 mmol), gave (14cc) 12.5 g (64.6%). m.p.114–116° C.;

TLC/R$_f$=0.64(A);

$^1$HNMR(CDCl$_3$): δ 1.22 (t, J=7.02 Hz, —OCH$_2$CH$_3$), 2.00 (s, 3H, —COCH$_3$), 3.22 (m, 2H, β-H), 4.19 (q, J=7.02

Hz, 2H—OCH$_2$CH$_3$), 4.88 (q, 1H, α-H), 6.14 (s, 1H, α-NH), 7.27–8.03 (m, 3H, Ar—H);

IR 3334 (NH), 2989 (CH), 1517 (CH, —C$_6$H$_5$), 1732 (C=O, COOEt), 1640 (C=O, NHCOCH$_3$), 913, 843, 800, 744 (2-CH$_3$-4-NO$_2$—C$_6$H$_5$).

Anal. Calcd. For C$_{14}$H$_{18}$N$_2$O$_5$: C, 57.14; H, 6.16; N, 9.52. Found: C, 56.99; H, 6.19; N, 9.48.

PREPARATION EXAMPLE 15

Synthesis of Phe(4-COOH)OH and It's Derivatives 15.1 D,L-Phe(4-COOH)OH (15aa)

To 68.0 g (0.5 mol)$_4$-Carboxyl-aniline dissolved in 40.0 g (0.29 mol) K$_2$CO$_3$/H$_2$O (200 ml) was added 35 g (0.507 mol)NaNO$_2$ with stirring, give a reddish solution. 500 ml concn. HCl/200 mlH$_2$O was cooled to –5° C. with stirring, added the above reddish solution, the internal temperature being maintained below –5° C., 0.5 g urea was added after 20 min. Continued stirring for 20 min., then added 30.0 g CH$_3$COONa, dissolved, gave a bright yellowish diazoate solution. Introduced the mixture of 75 mlCH$_2$=CHCOOH 100 ml acetone and 18 g CuCl$_2$.H$_2$O/50 mlH$_2$O that pre-prepared to the above diazoate solution, when the temperature reaches to 50–80° C. slowly, it produced gas. when the gas over, cooled, gave a great amount of slightly reddish precipitates, the precipitate was filtered off and sealed with ammonia water for 9 months at room temperature. The insoluble substance was filtered off and the filtrate was concentrated, acidified to PH4, the crystals that separated were collected and dried, gave the crude product (15aa) about 84.8 g.

15.2 D,L-Phe(4-COOCH$_2$CH$_3$)OCH$_2$CH$_3$HCl (15bb)

Method was same as (3bb). Added the above crude product (15aa) 84.8 g, gave 60.0 g (40.1%, cal. by 4-Carboxyl-aniline) (15bb). m.p. 137–139° C. FAB/MS m/z 266 (M+1-HCl)

15.3 D,L-N-AC-Phe(4-COOCH$_2$CH$_3$) OCH$_2$CH$_3$ (15cc)

Method was same as (3cc). Added (15bb) 40.0 g (0.133 mol), gave (15cc) 34.0 g (83.5%). m.p.89.5–90.5° C.; TLC/R$_f$=0.64(A);

$^1$HNMR(CDCl$_3$): δ 1.25 (t, J=7.02 Hz, —OCH$_2$CH$_3$), 1.38 (t, J=7.02 Hz, 3H, Ar—OCH$_2$CH$_3$), 2.00 (s, 3H, —OCH$_3$), 3.18 (m, 2H, β-H), 4.36 (q, J=7.02 Hz, 2H, Ar—OCH$_2$CH$_3$), 4.88 (m, 1H, α-H), 5.99 (d, 1H, α-NH), 7.1–7.98 (m, 4H, Ar—H);

IR 3247 (NH), 2989, 3075 (CH), 1738, 1707 (C=O, COOEt), 1646 (C=O, NHCOCH$_3$), 855, 766 (4-COOH—C$_6$H$_5$).

Anal. Calcd. For C$_{16}$H$_{21}$NO$_5$: C, 62.53; H, 6.89; N, 4.56. Found: C, 62.56; H, 6.85; N, 4.46.

PREPARATION EXAMPLE 16

Synthesis of Phe(3-COOH)OH and It's Derivatives 16.1 D,L-Phe(3-COOH)OH (16aa)

3-Carboxyl-aniline 100 g (0.73 mol) was aminolysised for 4 days at 70–80° C., concentrated to 100 ml under reduced pressure, and then acidified to PH3 with conc. HCl. The crystals that separated were collected and dried, gave the crude product (16aa) about 92.6 g.

16.2 D,L Phe(3-COOCH$_2$CH$_3$)OCH$_2$CH$_3$.HCl (16bb)

Method was same as (3bb). Added the above crude product (16aa) 92.6 g, gave 65.0 g (29.5%, cal. by 3-Carboxyl-aniline) (16bb). m.p. 165–167° C. FAB/MS m/z 266.1(M+1-HCl).

$^1$HNMR(CDCl$_3$): δ 1.29 (t, J=7.12 Hz, —OCH$_2$CH$_3$), 1.42 (t, J=7.08 Hz, 3H, Ar—OCH$_2$CH$_3$), 3.25 (m, 2H, β-H), 4.39 (q, J=7.02 Hz, 2H, Ar—OCH$_2$CH$_3$), 5.02 (m, 1H, α-H), 6.09 (d, 1H, α-NH), 7.21–8.08 (m, 4H, Ar—H);

Anal. Calcd. For C$_{14}$H$_{20}$NclO$_4$: C, 55.72; H, 6.68; N, 4.64. Found: C, 55.78; H, 6.62; N, 4.62.

16.3 D,L-N-AC-Phe(3-COOCH$_2$CH$_3$)OCH$_2$CH$_3$ (16cc)

Method was same as (3cc). Added (16bb) 54.0 g (0.18 mol), gave (16cc) 54.5 g (99.1%). Red oil residue, used for resolution.

EXAMPLE 17

Synthesis of Phe(2-COOH)OH and It's Derivatives 17.1 D,L-Phe(2-COOH)OH (17aa)

2-carboxyl-aniline 100 g (0.73 mol) was aminolysised for 4 days at 50° C., concentrated to 100 ml under reduced pressure, and then acidified to PH3 with conc. HCl. The crystals that separated were collected and dried, gave the crude product (17aa) about 88.6 g.

17.2 D,L-2-carboethoxydihydroisocarbostyril (17bb)

Method was same as (3bb). Added the above crude product (17aa) 88.6 g, gave 74.0 g (46.3%, cal. by 2-carboxyl-aniline) (17bb). m.p. 87–89° C. FAB/MS m/z 221 (M+2)

$^1$HNMR(CDCl$_3$): δ 1.15 (t, J=7.01 Hz, —OCH$_2$CH$_3$), 3.24–3.45 (m, 2H, β-H), 4.15 (m, J=7.08 Hz, 2H, —OCH$_2$CH$_3$), 5.13 (m, J=5.49 Hz, 1H, α-H), 7.22–8.08 (m, 4H, Ar—H); IR 3445 (NH), 2989 (CH), 1750 (C=O, COOEt), 1726 (C=O, —NHCO—), 1553, 1498 (CH, —C$_6$H$_5$), 757 (O—CO—C$_6$H$_5$).

Anal. Calcd. For C$_{12}$H$_{13}$NO$_3$: C, 65.74; H, 5.98; N, 6.39. Found: C, 65.78; H, 6.02; N, 6.35.

PREPARATION EXAMPLE 18

Resolution of D,L-N-AC-Phe(3-NO$_2$)OCH$_2$CH$_3$ 18.1 D-N-AC-Phe(3-NO$_2$)OCH$_2$CH$_3$ (1AA)

To a suspension of 16.3 g D,L-N-AC-Phe(3-NO$_2$) OCH$_2$CH$_3$ in 200 ml phosphate buffer (0.1M KH$_2$PO$_4$ and K$_2$HPO$_4$), maintained the temperature at 37° C., adjusted to PH7.4 with 1M NaOH, 20.0 mg α-Chymotrypsin was added, the reaction mixture was stirred by a magnetic stirrer and the pH was kept constant at about 7.4 with 2M KOH, stirred for 2 hr. The mixture was extracted with EtOAC (3×100 ml), the combined extract was washed with saturated NaCl once, dried with anhydrous Na$_2$SO$_4$, evaporated, crystallized from petroleum ether, gave a slightly yellow crystal, filter off, obtained (1AA) 7.8 g (95.7%), m.p.109–110° C., $[α]_D^{27}$=−9.90° (c=1.02, anhydrous MeOH).

18.2 L-N-AC-Phe(3-NO$_2$)OH (1BB)

The above aqueous solution was acidified to pH 2–3 with conc. HCl, the acidic solution was extracted with EtOAC (3×100 ml). The combined extract was washed with saturated NaCl once, dried with anhydrous Na$_2$SO$_4$, evaporated under reduced pressure below 40° C., gave a slightly yellowish solid (1BB) 6.8 g (92.7%), m.p.167–169° C., $[α]_D^{27}$=+31.9° (c=1.01, anhydrous MeOH).

18.3 D-Phe(3-NO$_2$)OH.HCl (1CC)

5.00 g (18 mmol) (1AA) in 100 ml 6M HCl was refluxed for 6 hr. Evaporated under reduced pressure to dryness, concentrated with anhydrous ethanol once, added 50 ml EtOAC, the solid was filtered off, gave slightly yellowish needles (1CC) 4.38 g (99.8%), m.p.241–243° C. (decomposed), $[α]_D^{25}$=−9.40° (c=1.05, anhydrous MeOH).

18.4 L-Phe(3-NO$_2$)OH.HCl (1DD)

(1BB) 5.00 g (20 mmol) as treated above, gave white needles (1DD) 4.65 g (95.1%), m.p.229–232° C. (decomposed), $[α]_D^{25}$=+8.0° (c=1.01, anhydrous MeOH).

18.5 D-N-AC-Phe(3-NO$_2$)OH (1EE)

(1AA) 1.00 g dissolved in 10 ml methanol, added 3 ml KOH solution under the cooling with stirring for 20 min.

The mixture was adjusted to pH 8.0 with 1M HCl, evaporated to dryness under reduced pressure below 40° C. Then the residue dissolved with 15 ml $H_2O$, acidified to pH2–3 with 1M HCl, the acidic solution was extracted with EtOAC (3×20 ml), the combined extract was dried with anhydrous $Na_2SO_4$, evaporated under reduced pressure, gave a slightly yellowish solid (1EE) 0.88 g (98.0%), m.p.162–164° C., $[\alpha]_D^{20}=-33.9°$ (c=1.27, anhydrous MeOH).

18.6 D-Phe(3-$NO_2$)$OCH_3$.HCl (1FF)

1.00 g (1CC) and $SOCl_2$/MeOH method. gave (1FF) 1.05 g (99.3%), m.p.174–176° C., $[\alpha]_D^{20}=-13.5°$ (c=0.88, anhydrous MeOH).

18.7 L-Phe(3-$NO_2$)$OCH_3$.HCl (1GG)

1.00 g (DD) and $SOCl_2$/MeOH method. gave (1GG) 1.05 g (99.4%), m.p.170–172° C., $[\alpha]_D^{20}=+14.1°$ (c=1.02, anhydrous MeOH).

PREPARATION EXAMPLE 19

Resolution of D,L-N-AC-Phe(2-F)$OCH_2CH_3$ 19.1 D-N-AC-Phe(2-F)$OCH_2CH_3$ (2AA)

Method was same as (1AA). D,L-N-AC-Phe(2-F)$OCH_2CH_3$ 12.16 g (47.7 mmol), gave colorless oil (2AA) 5.5 g (90.5%).

19.2 L-N-AC-Phe(2-F)OH (2BB)

Method was same as (1BB). Gave white solid (2BB) 4.76 g (88.0%). m.p.163–165° C., $[\alpha]_D^{20}=+33.9°$ (c=1.28, anhydrous MeOH).

19.3 D-Phe(2-F)OH.HCl (2CC)

Method was same as (1CC). (2AA) 4.73 g (18.7 mmol), gave white solid (2CC) 4.01 g (97.7%). m.p.215–218° C., $[\alpha]_D^{20}=-12.2°$ (c=1.02, anhydrous MeOH).

19.4 L-Phe(2-F)OH.HCl (2DD)

Method was same as (1DD). (2BB) 4.20 g (18.7 mmol), gave white needles (2DD) 4.09 g (99.8%), m.p.221–223° C., $[\alpha]_D^{25}=+14.5°$ (c=1.02, anhydrous MeOH).

19.5 D-N-AC-Phe(2-F)OH (2EE)

Method was same as (1EE). (2AA) 1.00 g (3.96 mmol), gave white solid (2EE) 0.65 g (73.1%), m.p.156–159° C., $[\alpha]_D^{20}=-37.9°$ (c=1.02, anhydrous MeOH).

19.6 D-Phe(2-F)$OCH_3$.HCl (2FF)

1.00 g (2CC) and $SOCl_2$/MeOH method, gave (2FF) 0.88 g (89.5%), m.p.176–178° C., $[\alpha]_D^{20}=-25.54°$ (c=1.21, anhydrous MeOH).

19.7 L-Phe(2-F)$OCH_3$.HCl (2GG)

1.00 g (2DD) and $SOCl_2$/MeOH method, gave (2GG) 0.97 g (98.6%), m.p.176–177° C., $[\alpha]_D^{20}=+29.33°$ (c=0.75, anhydrous MeOH).

PREPARATION EXAMPLE 20

Resolution of D,L-N-AC-Phe(3-F)$OCH_2CH_3$ 20.1 D-N-AC-Phe(3-F)$OCH_2CH_3$ (3AA)

Method was same as (1AA). D,L-N-AC-Phe(3-F)$OCH_2CH_3$ 15.28 g (62.5 mmol), gave colorless needles (3AA) 5.5 g (91.5%). m.p.107–108° C., $[\alpha]_D^{25}=-8.14°$ (c=1.02, anhydrous MeOH).

20.2 L-N-AC-Phe(3-F)OH (3BB)

Method was same as (1BB). Obtaining white solid (3BB) 6.71 g (95.4%). m.p.151–154° C., $[\alpha]_D^{25}=+31.59°$ (c=0.997, anhydrous MeOH).

20.3 D-Phe(3-F)OH.HCl (3CC)

Method was same as (1CC). (3AA) 5.00 g (19.8 mmol), gave white solid (3CC) 4.32 g (99.6%). m.p.237–239° C. (decomposed), $[\alpha]_D^{25}=-2.5°$ (c=1.00, anhydrous MeOH).

20.4 L-Phe(3-F)OH.HCl (3DD)

Method was same as (1DD). 5.00 g (3BB) was used, gave white solid (3DD) 4.91 g (99.3%), m.p.>241° C. (decomposed), $[\alpha]_D^{25}=+3.7°$ (c=1.00, anhydrous MeOH).

20.5 D-N-AC-Phe(3-F)OH (3EE)

Method was same as (1EE). (3AA) 1.00 g (3.96 mmol), gave white solid (2EE) 0.87 g (97.8%), m.p.152–154° C., $[\alpha]_D^{20}=-33.6°$ (c=1.19, anhydrous MeOH).

20.6 D-Phe(3-F)$OCH_3$.HCl (3FF)

1.00 g (3CC) and $SOCl_2$/MeOH method gave (3FF) 1.05 g (98.7%), m.p.151–153° C., $[\alpha]_D^{20}=-12.52°$ (c=1.07, anhydrous MeOH).

20.7 L-Phe(3-F)$OCH_3$.HCl (3GG)

1.00 g (3DD) and $SOCl_2$/MeOH method gave (3GG) 1.05 g (98.7%), m.p.175.5–177.5° C., $[\alpha]_D^{20}=+13.73°$ (c=0.75, anhydrous MeOH).

PREPARATION EXAMPLE 21

Resolution of D,L-N-AC-Phe(4-F)$OCH_2CH_3$ 21.1 D-N-AC-Phe(4-F)$OCH_2CH_3$ (4AA)

Method was same as (1AA). D,L-N-AC-Phe(4-F)$OCH_2CH_3$ 37.43 g (148 mmol), gave colorless needles (4AA) 16.60 g (88.7%). m.p.64–66° C., $[\alpha]_D^{25}=-8.24°$ (c=1.02, anhydrous MeOH).

21.2 L-N-AC-Phe(4-F)OH (4BB)

Method was same as (1BB). Gave white solid (4BB) 16.71 g (99.9%). m.p.133–136° C., $[\alpha]_D^{25}=+28.8°$ (c=1.00, anhydrous MeOH).

21.3 D-Phe(4-F)OH.HCl (4CC)

Method was same as (1CC). (4AA) 5.00 g (19.8 mmol), gave white solid (4CC) 4.23 g (97.5%). m.p.238–240° C. (decomposed), $[\alpha]_D^{25}=-5.9°$ (c=1.00, anhydrous MeOH).

21.4 L-Phe(4-F)OH.HCl (4DD)

Method was same as (1DD). 5.00 g (4BB), gave white solid (3DD) 4.88 g (100%), m.p.242–244° C. (decomposed), $[\alpha]_D^{25}=+2.9°$ (c=0.988, anhydrous MeOH).

21.5 D-N-AC-Phe(4-F)OH (4EE)

Method was same as (1EE). (4AA)1.00 g (3.96 mmol), gave white solid (4EE) 0.84 g (94.4%), m.p.139–142° C., $[\alpha]_D^{20}=-34.0°$ (c=1.20, anhydrous MeOH).

21.6 D-Phe(4-F)$OCH_3$.HCl (4FF)

1.00 g (4CC) and $SOCl_2$/MeOH method. gave (4FF) 1.06 g (100%), m.p.190–192° C., $[\alpha]_D^{20}=-15.67°$ (c=1.04, anhydrous MeOH).

21.7 L-Phe(4-F)$OCH_3$.HCl (4GG)

1.00 g (4DD) and $SOCl_2$/MeOH method. gave (4GG) 1.06 g (100%), m.p.185–187° C., $[\alpha]_D^{20}=+14.76°$ (c=1.14, anhydrous MeOH).

PREPARATION EXAMPLE 22

Resolution of D,L-N-AC-Phe(2-Cl)$OCH_2CH_3$ 22.1 D-N-AC-Phe(2-CL)$OCH_2CH_3$ (5AA)

Method was same as (1AA). D,L-N-AC-Phe(2-Cl)$OCH_2CH_3$ 10.9 g (37 mmol), gave white needles (5AA) 4.7 g (94.0%). m.p.87–88° C., $[\alpha]_D^{25}=+10.6°$ (c=0.99, anhydrous MeOH).

22.2 L-N-AC-Phe(2-Cl)OH (5BB)

Method was same as (1BB). obtaining white solid (5BB) 4.17 g (93.0%). m.p.166–1$^{67}$° C., $[\alpha]_D^{25}=-12.2°$ (c=1.02, anhydrous MeOH).

22.3 D-Phe(2-Cl)OH.HCl (5CC)

Method was same as (1CC). (5AA) 3.47 g (12.87 mmol), gave white solid (5CC) 2.97 g (97.7%). m.p.233–236° C. (decomposed), $[\alpha]_D^{25}=+15.9°$ (c=1.02, anhydrous MeOH).

22.4 L-Phe(2-Cl)OH (5DD)

Method was same as (1DD). 3.97 g (5BB), gave white solid (3DD) 3.80 g (99.4%), m.p.243–247° C. (decomposed), $[\alpha]_D^{25}=-17.3°$ (c=1.01, anhydrous MeOH).

22.5 D-N-AC-Phe(2-Cl)OH (5EE)

Method was same as (1EE). (5AA) 1.00 g (3.7 mmol), gave white solid (5EE) 0.87 g (97.1%), m.p.165–167° C., $[\alpha]_D^{20}=+11.8°$ (c=1.26, anhydrous MeOH).

22.6 D-Phe(2-Cl)OCH$_3$.HCl (5FF)

1.00 g (5CC) and SOCl$_2$/MeOH method. gave (5FF) 1.05 g (99.1%), m.p.147–149° C., $[\alpha]_D^{20}=+28.3°$ (c=1.04, anhydrous MeOH).

22.7 L-Phe(2-Cl)OCH$_3$.HCl (5GG)

1.00 g (5DD) and SOCl$_2$/MeOH method. gave (5GG) 1.06 g (100%), m.p.144–146° C., $[\alpha]_D^{20}=-29.64°$ (c=0.685, anhydrous MeOH).

PREPARATION EXAMPLE 23

Resolution of D,L-N-AC-Phe(3-Cl)OCH$_2$CH$_3$ 23.1 D-N-AC-Phe(3-Cl)OCH$_2$CH$_3$ (6AA)

Method was same as (1AA). D,L-N-AC-Phe(3-Cl)OCH$_2$CH$_3$ 16.5 g (61.05 mmol), gave white needles (6AA) 6.67 g (80.7%). m.p.70–72° C., $[\alpha]_D^{25}=-5.8°$ (c=1.03, anhydrous MeOH).

23.2 L-N-AC-Phe(3-Cl)OH (6BB)

Method was same as (1BB). Gave white solid (5BB) 6.30 g (85.2%). m.p.155–157° C., $[\alpha]_D^{25}=+35.2°$ (c=1.01, anhydrous MeOH).

23.3 D-Phe(3-Cl)OH.HCl (6CC)

Method was same as (1CC). (6AA) 5.17 g (19.18 mmol), gave white solid (6CC) 4.29 g (94.8%). m.p.239–242° C. (decomposed), $[\alpha]_D^{25}=-6.4°$ (c=1.01, anhydrous MeOH).

23.4 L-Phe(3-Cl)OH.HCl (6DD)

Method was same as (1DD). 5.38 g (6BB), gave white solid (6DD) 5.06 g (96.2%), m.p.244–247° C. (decomposed), $[\alpha]_D^{25}=+6.7°$ (c=1.01, anhydrous MeOH).

23.5 D-N-AC-Phe(3-Cl)OH (6EE)

Method was same as (1EE). (6AA) 1.00 g (3.7 mmol), gave white solid (6EE) 0.85 g (94.9%), m.p.151–153° C., $[\alpha]_D^{20}=-29.4°$ (c=1.02, anhydrous MeOH).

23.6 D-Phe(3-Cl)OCH$_3$.HCl (6FF)

1.00 g (6CC) and SOCl$_2$/MeOH method. gave (6FF) 0.80 g (75.5%), m.p.122–123° C., $[\alpha]_D^{20}=-12.27°$ (c=0.92, anhydrous MeOH).

23.7 L-Phe(3-Cl)OCH$_3$.HCl (6GG)

1.00 g (6DD) and SOCl$_2$/MeOH method. gave (6GG) 1.06 g (100%), m.p.120–122° C., $[\alpha]_D^{20}=+13.14°$ (c=0.845, anhydrous MeOH).

PREPARATION EXAMPLE 24

Resolution of D,L-N-AC-Phe(4-Br)OCH$_2$CH$_3$ 24.1 D-N-AC-Phe(4-Br)OCH$_2$CH$_3$ (7AA)

Method was same as (1AA). D,L-N-AC-Phe(4-Br)OCH$_2$CH$_3$ 20.0 g (63.5 mmol), gave white needles (7AA) 9.41 g (94.1%). m.p.96–98° C., $[\alpha]_D^{25}=-20.0°$ (c=1.03, anhydrous MeOH). Subtilisin carsberg was used.

24.2 L-N-AC-Phe(4-Br)OH (7BB)

Method was same as (1BB). Gave needles (6BB) 9.17 g (100.7%). m.p.158–160° C., $[\alpha]_D^{25}=+39.9°$ (c=1.02, anhydrous MeOH).

24.3 D-Phe(4-Br)OH.HCl (7CC)

Method was same as (1CC). (7AA) 5.00 g (16.0 mmol), gave white solid (7CC) 4.33 g (96.9%). m.p.244–247° C. (decomposed), $[\alpha]_D^{25}=-4.90°$ (c=1.01, anhydrous MeOH).

24.4 L-Phe(4-Br)OH.HCl (7DD)

Method was same as (1DD). 9.15 g (7BB), gave white solid (7DD) 8.67 g (96.6%), m.p.244–247° C. (decomposed), $[\alpha]_D^{25}=+4.75°$ (c=0.998, anhydrous MeOH).

24.5 D-N-AC-Phe(4-Br)OH (7EE)

Method was same as (1EE). (7AA) 1.00 g (3.2 mmol), gave white solid (7EE) 0.87 g (95.6%), m.p.152–154° C., $[\alpha]_D^{20}=-37.9°$ (c=1.00, anhydrous MeOH).

24.6 D-Phe(4-Br)—OCH$_3$.HCl (7FF)

1.00 g (7CC) and SOCl$_2$/MeOH method. gave (7FF) 1.01 g (96.2%), m.p.198–200° C., $[\alpha]_D^{20}=-16.02°$ (c=1.33, anhydrous MeOH).

24.7 L-Phe(4-Br)OCH$_3$.HCl (7GG)

1.00 g (7DD) and SOCl$_2$/MeOH method. gave (7GG) 1.05 g (99.9%), m.p.190–192° C., $[\alpha]_D^{20}=+22.88°$ (c=0.75, anhydrous MeOH).

PREPARATION EXAMPLE 25

Resolution of D,L-N-AC-Phe(4-F-3-Cl)OCH$_2$CH$_3$ 25.1 D-N-AC-Phe(4-F-3-Cl)OCH$_2$CH$_3$ (8AA)

Method was same as (1AA). D,L-N-AC-Phe(4-F-3-Cl)OCH$_2$CH$_3$ 17.6 g (61 mmol), gave colorless needles (8AA) 8.04 g (91.4%). m.p. 92–94° C., $[\alpha]_D^{20}=-7.16°$ (c=1.145, anhydrous MeOH).

25.2 L-N-AC-Phe(4-F-3-Cl)OH (8BB)

Method was same as (1BB). Gave white solid (8BB) 7.26 g (91.4%). m.p. 163–165° C., $[\alpha]_D^{20}=+33.33°$ (c=0.96, anhydrous MeOH).

25.3 D-Phe(4-F-3-Cl)OH.HCl (8CC)

Method was same as (1CC). (8AA) 5.00 g (17.4 mmol), gave white solid (8CC) 4.18 g (94.6%).

m.p. 230–232° C. (decomposed), $[\alpha]_D^{25}=-6.50°$ (c=1.02, anhydrous MeOH).

25.4 L-Phe(4-F-3-Cl)OH.HCl (8DD)

Method was same as (1DD). 5.00 g (8BB), gave white needles (8DD) 4.76 g (97.3%), m.p.233–237° C. (decomposed), $[\alpha]_D^{25}=+6.4°$ (c=1.01, anhydrous MeOH).

25.5 D-N-AC-Phe(4-F-3-Cl)OH (8EE)

Method was same as (1EE). (8AA) 1.00 g (3.48 mmol), gave white solid (8EE) 0.87 g (96.4%), m.p.160–163° C., $[\alpha]_D^{20}=-32.4°$ (c=1.27, anhydrous MeOH).

25.6 D-Phe(4-F-3-Cl)OCH$_3$.HCl (8FF)

3.00 g (8CC) and SOCl$_2$/MeOH method. Gave (8FF) 2.89 g (91.3%), m.p.178–182° C., $[\alpha]_D^2=-12.4°$ (c=1.12, anhydrous MeOH).

25.7 L-Phe(4-F-3-Cl)OCH$_3$.HCl (8GG)

1.00 g (8DD) and SOCl$_2$/MeOH method. Gave (8GG) 1.08 g (99.9%), m.p.182–183° C., $[\alpha]_D^{20}=+13.81°$ (c=1.00, anhydrous MeOH).

PREPARATION EXAMPLE 26

Resolution of D,L-N-AC-Phe(2,4-di-Cl)OCH$_2$CH$_3$ 26.1 D-N-AC-Phe(2,4-di-Cl)OCH$_2$CH$_3$ (9AA)

Method was same as (1AA). D,L-N-AC-Phe(2,4-di-Cl)OCH$_2$CH$_3$ 5.0 g (16.34 mmol), gave colorless needles (9AA) 2.34 g (93.6%). m.p.89–91° C., $[\alpha]_D^{25}=+7.0°$ (c=1.00, anhydrous MeOH). Subtilisin carsberg was used.

26.2 L-N-AC-Phe(2,4-di-Cl)OH (9BB)

Method was same as (1BB). Gave white needles (9BB) 2.28 g (100.4%). m.p.177–179° C., $[\alpha]_D^{25}=-20.5°$ (c=1.00, anhydrous MeOH).

26.3 D-Phe(2,4-di-Cl)OH.HCl (9CC)

Method was same as (1CC). (9AA) 1.75 g (5.76 mmol), gave white solid (9CC) 1.51 g (97.0%). m.p.240–241° C. (decomposed), $[\alpha]_D^{25}=-9.29°$ (c=1.02, anhydrous MeOH).

26.4 L-Phe(4-F-3-Cl)OH.HCl (9DD)

Method was same as (1DD). 2.47 g (9BB), gave white solid (9DD) 2.67 g (96.6%), m.p.244–247° C. (decomposed), $[\alpha]_D^{25}$=+9.00° (c=0.995, anhydrous MeOH).

26.5 D,L-N-AC-Phe(2,4-di-Cl)OH (9EE)

Method was same as (1EE). D,L-N-AC-Phe(2,4-diCl)OCH$_2$CH$_3$ 1.00 g (3.29 mmol), gave white solid (9EE) 0.908 g (95.3%), m.p.132–135° C., 26.6 D-Phe(2,4-di-Cl)OCH$_2$CH$_3$.HCl (9FF)

1.00 g (9CC) and SOCl$_2$/EtOH method. gave (9FF) 1.07 g (97.0%), m.p.133–134° C., $[\alpha]_D^{20}$=−29.6° (c=1.50, anhydrous MeOH).

26.7 L-Phe(2,4-di-Cl)OCH$_3$.HCl (9GG)

1.00 g (9DD) and SOCl$_2$/MeOH method, gave (9GG) 1.03 g (98.0%), m.p.175–178° C., $[\alpha]_D^{20}$=+16.86° (c=0.80, anhydrous MeOH).

PREPARATION EXAMPLE 27

Resolution of D,L-N-AC-Phe(2,5-di-Cl)OCH$_2$CH$_3$ 27.1 D-N-AC-Phe(2,5-di-Cl)OCH$_2$CH$_3$ (10AA)

Method was same as (1AA). D,L-N-AC-Phe(2,5-di-Cl)OCH$_2$CH$_3$ 18.0 g (59.2 mmol), gave colorless needles (10 μM) 8.80 g (97.8%). m.p.125–126° C., $[\alpha]_D^{25}$=−14.45° (c=1.04, anhydrous MeOH).

27.2 L-N-AC-Phe(2,5-di-Cl)OH (10BB)

Method was same as (1BB). Gave colorless needles (10BB) 7.97 g (97.4%). m.p.179–181° C., $[\alpha]_D^{25}$=+14.27° (c=1.08, anhydrous MeOH).

27.3 D-Phe(2,5-di-Cl)OH.HCl (10CC)

Method was same as (1CC). (10AA) 4.00 g (13.16 mmol), gave white solid (10CC) 3.54 g (99.5%). m.p.227–230° C. (decomposed),$[\alpha]_D^{25}$=−25.7° (c=1.05, anhydrous MeOH).

27.4 L-Phe(2,5-di-Cl)OH.HCl (10DD)

Method was same as (1DD). 5.00 g (10BB), gave white needles (10DD) 4.82 g (98.4%), m.p.225–227° C. (decomposed), $[\alpha]_D^{25}$=+23.00° (c=0.995, anhydrous MeOH).

27.5 D-N-AC-Phe(2,5-di-Cl)OH (10EE)

Method was same as (1EE). (10AA) 1.00 g (3.29 mmol), gave white solid (10EE) 0.86 g (94.7%), m.p.176–178° C., $[\alpha]_D^{25}$=−15.93° (c=0.999, anhydrous MeOH).

27.6 D-Phe(2,5-di-Cl)OCH$_2$CH$_3$.HCl (10FF)

1.00 g (10CC) and SOCl$_2$/EtOH method. gave (10FF) 1.10 g (99.7%), m.p.157–159° C., $[\alpha]_D^{20}$=−24.72° (c=1.06, anhydrous MeOH).

27.7 L-Phe(2,5-di-Cl)OCH$_3$.HCl (10GG)

1.00 g (10DD) and SOCl$_2$/MeOH method. gave (10GG) 1.05 g (99.9%), m.p.182–183° C., $[\alpha]_D^{20}$=+32.7° (c=0.85, anhydrous MeOH).

PREPARATION EXAMPLE 28

Resolution of D,L-N-AC-Phe(3,4-di-Cl)OCH$_2$CH$_3$ 28.1 D-N-AC-Phe(3,4-di-Cl)OCH$_2$CH$_3$ (11AA)

Method was same as (1AA). D,L-N-AC-Phe(3,4-di-Cl)OCH$_2$CH$_3$ 7.7 g (26.6 mmol), gave white solid (11AA) 3.46 g (89.9%). m.p.122–124° C., $[\alpha]_D^{25}$=−23.8° (c=1.16, anhydrous MeOH).

28.2 L-N-AC-Phe(3,4-di-Cl)OH (11BB)

Method was same as (1BB). Gave white solid (11BB) 3.44 g (93.9%), m.p.149–151° C., $[\alpha]_D^{25}$=+43.2° (c=1.01, anhydrous MeOH).

PREPARATION EXAMPLE 29

Resolution of D,L-N-AC-Phe(2-CH$_3$-3-Cl)OCH$_2$CH$_3$ 29.1 D-N-AC-Phe(2-CH$_3$-3-Cl)OCH$_2$CH$_3$ (13AA)

Method was same as (1AA). D,L-N-AC-Phe(2-CH$_3$-3-Cl)OCH$_2$CH$_3$ 19.0 g (67.02 mmol), gave colorless needles (13AA) 9.22 g (92.0%). m.p.130–132° C., $[\alpha]_D^{25}$=+9.40° (c=1.165, anhydrous MeOH).

29.2 L-N-AC-Phe(2-CH$_3$-3-Cl)OH (13BB)

Method was same as (1BB). Gave colorless needles (13BB) 7.74 g (90.0%). m.p.174–176° C., $[\alpha]_D^{25}$=−11.86° (c=1.265, anhydrous MeOH).

29.3 D-Phe(2-CH$_3$-3-Cl)OH.HCl (13CC)

Method was same as (1CC). (13AA) 2.00 g (7.05 mmol), gave white solid (13CC) 1.68 g (95.2%). m.p.224–227° C. (decomposed),$[\alpha]_D^{25}$=−5.18° (c=1.10, anhydrous MeOH).

29.4 L-Phe(2-CH$_3$-3-Cl)OH.HCl (13DD)

Method was same as (1DD). 2.00 g (13BB), gave white solid (13DD) 1.67 g (95.0%), m.p.222–225° C. (decomposed), $[\alpha]_D^{25}$=+6.03° (c=1.09, anhydrous MeOH).

29.5 D-N-AC-Phe(2-CH$_3$-3-Cl)OH (13EE)

Method was same as (1EE). (13AA) 1.00 g (3.53 mmol), gave white solid (13EE) 0.88 g (97.6%), m.p.173–175° C., $[\alpha]_D^{25}$=+10.35° (c=0.85, anhydrous MeOH).

29.6 D-Phe(2-CH$_3$-3-Cl)OCH$_2$CH$_3$.HCl (13FF)

1.00 g (13CC) and SOCl$_2$/EtOH method. gave (13FF) 1.08 g (97.1%), m.p.188–190° C., $[\alpha]_D^{20}$=−33.89° (c=0.95 anhydrous MeOH).

29.7 L-Phe(2-CH$_3$-3-Cl)OCH$_3$.HCl (13GG)

0.26 g (13DD) and SOCl$_2$/MeOH method. gave (13GG) 0.26 g (95.0%), m.p.174–176° C., $[\alpha]_D^{20}$=+31.75° (c=0.63, anhydrous MeOH).

PREPARATION EXAMPLE 30

Resolution of D,L-N-AC-Phe(4-COOC$_2$H$_5$)OCH$_2$CH$_3$ 30.1 D-N-AC-Phe(4-COOC$_2$H$_5$)OCH$_2$CH$_3$ (15AA)

Method was same as (1AA). D,L-N-AC-Phe(4-COOC$_2$H$_5$)OCH$_2$CH$_3$ 21.1 g (68.7 mmol), gave colorless needles (15AA) 10.3 g (97.6%). m.p.97–98° C., $[\alpha]_D^{25}$=+7.9° (c=1.00, anhydrous MeOH). Subtilisin carsberg was used 30.2 L-N-AC-Phe(4-COOC$_2$H$_5$)OH (15BB)

Method was same as (1BB). Gave colorless needles (15BB) 8.9 g (92.8%). m.p.174–175° C., $[\alpha]_D^{25}$=−6.37° (c=1.02, anhydrous MeOH).

30.3 D-Phe(4-COOH)OH.HCl (15CC)

Method was same as (1CC). (15AA) 4.07 g (13 mmol), gave white solid (15CC) 3.28 g (100%). m.p.>280° C. (decomposed), $[\alpha]_D^{20}$=−33.96° (c=1.96, DMSO).

30.4 L-Phe(4-COOH)OH.HCl (15DD)

Method was same as (1DD). 4.43 g (15BB), gave white solid (15DD) 3.87 g (99.3%), m.p.>280° C. (decomposed), $[\alpha]_D^{20}$=+29.72° (c=1.24, DMSO).

30.5 D-Phe(4-COOEt)OCH$_2$CH$_3$.HCl (15EE)

1.00 g (15CC) and SOCl$_2$/EtOH method. gave (15EE) 1.17 g (95.3%), m.p.138–140° C., $[\alpha]_D^{20}$=−15.02° (c=1.21, anhydrous MeOH).

30.6 L-Phe(4-COOCH$_3$)OCH$_3$.HCl (15FF)

1.00 g (15DD) and SOCl$_2$/MeOH method. gave (15FF) 1.03 g (92.4%), m.p.178–180° C., $[\alpha]_D^{20}$=+17.09° (c=1.11, anhydrous MeOH).

PREPARATION EXAMPLE 31

Resolution of D,L-N-AC-Phe(3-COOC$_2$H$_5$)OCH$_2$CH$_3$ 31.1 D-N-AC-Phe(3-COOC$_2$H$_5$)OCH$_2$CH$_3$ (16AA)
Method was same as (1AA). Used the product of (1.16.3) 55 g (0.18 mmol), gave oil (16AA).

31.2 L-N-AC-Phe(3-COOC$_2$H$_5$)OH (16BB)
Method was same as (1BB). Gave colorless needles (16BB) 23.0 g (92.0%). m.p. 148–149° C., $[\alpha]_D^{25}$=+39.37° (c=1.625, anhydrous MeOH).
IR 3321 (NH), 2989 (CH), 1707 (C=O, COOEt), 1615 (C=O, NHCOCH$_3$), 760, 704 (3-COOEt-C$_6$H$_5$), 1566 (CH, —C$_6$H$_5$)

31.3 D-Phe(3-COOH)OH.HCl (16CC)
Method was same as (1CC). gave white solid (16CC) 21.5 g (97.8%). m.p.265–270° C. (decomposed), $[\alpha]_D^{20}$=−26,656° (c=1.314, DMSO).

31.4 L-Phe(3-COOH)OH.HCl (16DD)
Method was same as (1DD). 1.00 g (16BB), gave white solid (16DD) 0.84 g (95.5%), m.p.270–272° C. (decomposed), $[\alpha]_D^{20}$=+28.03° (c=1.106, DMSO).

31.5 D-Phe(3-COOEt)OCH$_2$CH$_3$.HCl (16EE)
1.00 g (16CC) and SOCl$_2$/EtOH method. gave (16EE) 1.18 g (95.8%), m.p.192–194° C., $[\alpha]_D^{20}$=−13.02° (c=1.26, anhydrous MeOH).

31.6 L-Phe(3-COOCH$_3$)OCH$_3$.HCl (16FF)
1.00 g (16DD) and SOCl$_2$/MeOH method. gave (16FF) 1.08 g (92.4%), m.p.163–165° C., $[\alpha]_D^{20}$=+18.85° (c=0.96, anhydrous MeOH).

PREPARATION EXAMPLE 32

Resolution of D,L-2-carboethoxydihydroisocarbostyril 32.1 D-2-carboethoxydihydroisocarbostyril (17AA)
Method was same as (1AA). D,L-2-carboethoxydihydroisocarbostyril 10.0 g, gave (17AA) 4.55 g (91%). m.p.86–88° C., $[\alpha]_D^{20}$=+7.8° (c=1.16, anhydrous MeOH).

32.2 L-2-carboethoxydihydroisocarbostyril (17BB)
Method was same as (1BB). Gave (16BB) 4.15 g (95.2%). m.p.151–153° C., $[\alpha]_D^{20}$=5.5° (c=1.22, anhydrous MeOH).

EXAMPLE 1

Synthesis of HIM-CO-Leu-D-Trp-D-Phe(2-F)—OH

To a stirred solution of D-TrpOC$_2$H$_5$.HCl 135 mg (0.5 mmol) in 2 ml DMF was added NMM 0.06 ml (0.5 mmol) and 5 ml THF, dissolved, added HIM-CO-LeuOH 128 mg (0.5 mmol), then 81 mg HOBt (0.6 mmol) and 76 mg DIC (0.6 mmol) was added. The mixture was stirred for 4 hrs.

To a solution of D-Phe(2-F)OC$_2$H$_5$.HCl 124.0 mg (0.5 mmol) in 2 ml DMF was added NMM 0.06 ml (0.5 mmol) and 5 ml THF, dissolved, added all the above product, and then 81 mg HOBt (0.6 mmol) and 76 mg DIC (0.6 mmol) was added, stirred for 4 hr at room temperature. Evaporated, the residue was dissolved with EtOAc, organic layer was washed with H$_2$O, 0.5M HCl (10 ml), saturated NaHCO$_3$ (10 ml) and saturated NaCl (10 ml). The EtOAc was evaporated and gave colorless oil, re-crystallized from MeOH—H$_2$O, to afford crystals, collected the crystals. The above crystals dissolved in 2 ml MeOH, added 2 ml 1M NaOH under cooling and stirred for 1 hr at room temperature. The reaction mixture was acidified with 1 M HCl to about PH8.0, evaporated, added 20 ml H$_2$O, acidified with 1M HCl to pH 3.0, the crystals that separated were collected and dried, gave the title product about 250 mg. (79.6%). TLC R$_f$=0.54(CHCl$_3$:MeOH:HAC=9:1:0.5). FAB-MS m/z 629.3 (M+1), 651.3 (M+Na). HPLC R$_t$=14.44 min. (Flow: A 50%–0%, B 50%–100%/10 min. A 0%–50%, B 100%–50%/10–20 min., run at 1.00 ml/min.)

The condition of analysis by HPLC:

| | |
|---|---|
| Pump | Waters 600E |
| Column | Kromasil-C$_{18}$ 5 μm, 4.6 × 250 mm |
| Solvent gradient | A: 0.1% TFA/H$_2$O   B: 70% CH$_3$CN/0.1% TFA-H$_2$O |
| UV detector | Spectra-Physics UV1000, detected at 280 nm |

EXAMPLE 2–53

The tripeptides in Example 2–53 were prepared in a similar manner as Example 1. The tripeptides were all purified by HPLC and FAB was performed (Table 1)

TABLE 1 the MS and HPLC data of sample 1–53

| No. | Primary Structure | MS | HPLC R$_t$/purity (%) |
|---|---|---|---|
| 1 | HIM-CO—NH—CH$_2$—CO-D-Trp-D-Trp-OH | 587(M + 1) | 5.65/96.7%[d] |
| 2 | HIM-CO-GABA-D-Trp-D-Trp-OH | 601.1(M + 1) | 5.82/97.6%[d] |
| 3 | HIM-CO—NH—(CH$_2$)$_2$—CO-D-Trp-D-Trp-OH | 601.3(M + 1) | 6.45/99.2%[d] |
| 4 | HIM-CO-Leu-D-Trp-D-Phe(2-F)—OH | 608.3(M + 1) | 8.20/93.3%[d] |
| 5 | HIM-CO-Leu-D-Trp-D-Phe(3-F)—OH | 608.2(M + 1) | 8.53/94.5%[d] |
| 6 | HIM-CO-Leu-D-Trp-D-Phe(4-F)—OH | 608.2(M + 1) | 8.10/95.0%[d] |
| 7 | HIM-CO-Leu-D-Trp-D-Phe(2-Cl)—OH | 624.3(M + 1) | 8.23/100%[d] |
| 8 | HIM-CO-Leu-D-Trp-D-Phe(3-Cl)—OH | 623.2(M + 1) | 9.21/98.8%[d] |
| 9 | HIM-CO-Leu-D-Trp-D-Phe(4-Cl)—OH | 623.2(M + 1) | 9.93/100%[d] |
| 10 | HIM-CO-Leu-D-Trp-D-Phe(4-Br)—OH | 669.1(M + 1) | 8.77/94.5%[d] |
| 11 | HIM-CO-Leu-D-Trp-D-Phe(3-NO$_2$)—OH | 635.1(M + 1) | 8.07/99.1%[d] |
| 12 | HIM-CO-Leu-D-Trp-D-Phe(3-COOH)—OH | 690.2(M + 1)** | 8.47/89.5%[d] |
| 13 | HIM-CO-Leu-D-Trp-D-Phe(4-COOH)—OH | 690.4(M + 1)** | 7.37/95.1%[d] |
| 14 | HIM-CO-Leu-D-Trp-D-Phe(3-Cl-4-F)—OH | 656.3(M + 1)* | 9.83/98.2%[d] |
| 15 | HIM-CO-Leu-D-Trp-D-Phe(2,4-Cl)—OH | 659.1(M + 1) | 12.71/93.1%[d] |
| 16 | HIM-CO-Leu-D-Trp-D-Phe(2,5-Cl)—OH | 659.3(M + 1) | 12.01/100%[d] |
| 17 | HIM-CO-Leu-D-Trp-D-Phe(2-CH$_3$-3-Cl)—OH | 638.4(M + 1) | 18.11/100%[d] |
| 18 | HIM-CO-Leu-D-Phe(2-F)-D-Trp-OH | 622.0(M + 1)* | 9.12/95.8%[d] |

TABLE 1-continued the MS and HPLC data of sample 1–53

| | | | |
|---|---|---|---|
| 19 | HIM-CO-Leu-D-Phe(3-F)-D-Trp-OH | 622.1(M + 1)* | 8.69/97.7%[d] |
| 20 | HIM-CO-Leu-D-Phe(4-F)-D-Trp-OH | 622.1(M + 1)* | 8.86/98.0%[d] |
| 21 | HIM-CO-Leu-D-Phe(4-Br)-D-Trp-OH | 683.1(M + 1)* | 1.77/97.8%[d] |
| 22 | HIM-CO-Leu-D-Phe(3-NO$_2$)-D-Trp-OH | 649.2(M + 1)* | 9.59/99.0%[d] |
| 23 | HIM-CO-Leu-D-Phe(4-F-3-Cl)-D-Trp-OH | 656.4(M + 1)* | 13.01/98.0%[d] |
| 24 | HIM-CO-Leu-D-Phe(3-CO-D-Trp-OH)-D-Trp-OH | 848.2(M + 1)*** | 7.82/85.4%[d] |
| 25 | HIM-CO-Leu-D-Phe(4-CO-D-Trp-OH)-D-Trp-OH | 848.0(M + 1)*** | 8.26/96.4%[d] |
| 26 | HIM-CO-Leu-D-Phe(2-CH$_3$-3-Cl)-D-Trp-OH | 652.4(M + 1)* | 14.52/99.8%[d] |
| 27 | Phenoxy-CO-Pro-D-Trp-D-Phe(2-F)—OH | 601.3(M + 1)* | 4.83/95.0%[d] |
| 28 | Phenoxy-CO-Pro-D-Trp-D-Phe(3-F)—OH | 601.3(M + 1)* | 5.07/97.4%[d] |
| 29 | Phenoxy-CO-Pro-D-Trp-D-Phe(4-F)—OH | 601.3(M + 1)* | 4.58/99.0%[d] |
| 30 | Phenoxy-CO-Pro-D-Trp-D-Phe(2-Cl)—OH | 617.4(M + 1)* | 7.75/92.0%[d] |
| 31 | Phenoxy-CO-Pro-D-Trp-D-Phe(3-Cl)—OH | 617.2(M + 1)* | 5.42/98.3%[d] |
| 32 | Phenoxy-CO-Pro-D-Trp-D-Phe(4-Cl)—OH | 617.2(M + 1)* | 5.04/96.3%[d] |
| 33 | Phenoxy-CO-Pro-D-Trp-D-Phe(4-Br)—OH | 662.0(M + 1)* | 5.21/93.5%[d] |
| 34 | Phenoxy-CO-Pro-D-Trp-D-Phe(3-NO$_2$)—OH | 650.2(M + 1)* | 6.12/97.0%[d] |
| 35 | Phenoxy-CO-Pro-D-Trp-D-Phe(4-F-3-Cl)—OH | 635.2(M + 1)* | 5.18/95.3%[d] |
| 36 | Phenoxy-CO-Pro-D-Trp-D-Phe(2,4-Cl)—OH | 652.0(M + 1)* | 6.12/97.0%[d] |
| 37 | Phenoxy-CO-Pro-D-Trp-D-Phe(2,5-Cl)—OH | 652.1(M + 1)* | 7.57/96.4%[d] |
| 38 | Phenoxy-CO-Pro-D-Trp-D-Phe(3-COOH)—OH | 655.2(M + 1)** | 4.98/92.6%[d] |
| 39 | Phenoxy-CO-Pro-D-Trp-D-Phe(4-COOH)—OH | 655.0(M + 1)** | 5.05/96.8%[d] |
| 40 | Phenoxy-CO-Pro-D-Trp-D-Phe(2-CH$_3$-3-Cl)—OH | 631.4(M + 1)* | 6.91/97.4%[d] |
| 41 | o-CPh-D-Trp-D-Phe(2-F)—OH | 557.3(M + 1)* | 9.73/100%[c] |
| 42 | o-CPh-D-Trp-D-Phe(3-F)—OH | 557.1(M + 1)* | 9.63/94.0%[c] |
| 43 | o-CPh-D-Trp-D-Phe(4-F)—OH | 557.1(M + 1)* | 12.9/100%[c] |
| 44 | o-CPh-D-Trp-D-Phe(2-Cl)—OH | 573.0(M + 1)* | 9.22/92.7%[c] |
| 45 | o-CPh-D-Trp-D-Phe(3-Cl)—OH | 596.2(M + Na)* | 9.89/97.0%[c] |
| 46 | o-CPh-D-Trp-D-Phe(4-Cl)—OH | 573.2(M + 1)* | 7.17/98.0%[c] |
| 47 | o-CPh-D-Trp-D-Phe(4-Br)—OH | 618.1(M + 1)* | 7.70/98.0%[c] |
| 48 | o-CPh-D-Trp-D-Phe(3-NO$_2$)—OH | 584.0(M + 1)* | 5.22/100%[c] |
| 49 | o-CPh-D-Trp-D-Phe(3-COOH)—OH | 625.2(M + 1)** | 5.01/97.4%[c] |
| 50 | o-CPh-D-Trp-D-Phe(4-COOH)—OH | 625.0(M + 1)** | 5.06/98.4%[c] |
| 51 | o-CPh-D-Trp-D-Phe(2,4-Cl)—OH | 608.2(M + 1)* | 5.89/98.0%[c] |
| 52 | o-CPh-D-Trp-D-Phe(2,5-Cl)—OH | 608.2(M + 1)* | 5.01/99.0%[c] |
| 53 | o-CPh-D-Trp-D-Phe(2-CH$_3$—Cl)—OH | 587.2(M + 1)* | 5.97/98.0%[c] |

| | time(min.) | flow | A% | B% |
|---|---|---|---|---|
| a | 0 | 1 | 40 | 60 |
| | 10 | 1 | 0 | 100 |
| | 20 | 1 | 40 | 60 |
| b | 0 | 0.6 | 50 | 50 |
| | 10 | 1 | 0 | 100 |
| | 20 | 1 | 20 | 80 |
| c | 0 | 0.6 | 50 | 50 |
| | 10 | 1 | 0 | 100 |
| | 20 | 1 | 50 | 50 |
| d | 0 | 1 | 10 | 90 |
| | 10 | 1 | 0 | 100 |

*(Methyl ester before hydrolysis)
**(Diethyl ester before hydrolysis)
***(Dimethyl ester before hydrolysis)

Bioactivities of Peptides

Experimental Material

| | |
|---|---|
| Wistar rat | from the experimental animal center of Academy of Military Medical Sciences |
| ET-1 | American peptide company |
| 10% potassium carbonate | provide for ourselves |
| Improved Kreb's-Ringer buffer | provide for ourselves |

Experimental procedure peptide from

The quantitative samples (tripeptide from example 1–53) $2 \times 10^{-6}$ mol was dissolved in 0.5 ml 10% potassium carbonate and further diluted to a 5 ml-volumetric flask using improved Kreb's-Ringer buffer and the solution was stored in refrigerator. The different concentrations ($10^{-6}$, $10^{-7}$, $10^{-8}$, $10^{-9}$M) of the peptides were obtained by diluting the stored solutions using the buffer.

The artery from the chest of beheaded Wistar rat was put in culture container filled with blood vessel nutrition solution. The blood vessel was washed for eliminating its trace blood, and then separated from peripheral tissue, and was cut to give 3 mm-wide arterial rings. Two stainless wires with diameter of 0.1 mm through the arterial ring were linked separately to form a connective triangle. There was 10 ml blood vessel nutrition solution in a thermostatic container whose bottom was immobilized with one of the two triangles at 37° C. The container was continuously aerated with a mixed gas of 95% oxygen and 5% carbon dioxide. Another triangle in the upper was linked with the stand auto-balance recorder by inserting a tension-energy exchanger. Each arterial ring can bear a burden of 0.5 g. After the system was balanced and well distributed, the tripeptides were added into the system. 10 nM ET-1 was used to induce and contract the artery ring firstly, about 10 min., the tripeptides in a range of $10^{-9} \sim 10^{-6}$M were added into the system, the antagonistic effect against the contraction would be observed on the recorder. The test result is shown in following table.

|     |                                                      | Antagonistic effect(mol/l) | | | |
| --- | ---------------------------------------------------- | :---: | :---: | :---: | :---: |
| No. | Primary Structure                                    | $10^{-6}$ | $10^{-7}$ | $10^{-8}$ | $10^{-9}$ |
| 1   | HIM-CO—NH—CH$_2$-CO-D-Trp-D-Trp-OH                   |   |   |   | + + |
| 2   | HIM-CO-GABA-D-Trp-D-Trp-OH                           |   |   |   | +   |
| 3   | HIM-CO—NH—(CH$_2$)$_2$-CO-D-Trp-D-Trp-OH             |   |   |   | +   |
| 4   | HIM-CO-Leu-D-Trp-D-Phe(2-F)—OH                       |   |   |   | +   |
| 5   | HIM-CO-Leu-D-Trp-D-Phe(3-F)—OH                       |   |   |   | +   |
| 6   | HIM-CO-Leu-D-Trp-D-Phe(4-F)—OH                       |   |   | + |     |
| 7   | HIM-CO-Leu-D-Trp-D-Phe(2-Cl)—OH                      |   |   |   | +   |
| 8   | HIM-CO-Leu-D-Trp-D-Phe(3-Cl)—OH                      |   |   | + |     |
| 9   | HIM-CO-Leu-D-Trp-D-Phe(4-Cl)—OH                      |   |   |   | + + |
| 10  | HIM-CO-Leu-D-Trp-D-Phe(4-Br)—OH                      |   |   |   | +   |
| 11  | HIM-CO-Leu-D-Trp-D-Phe(3-NO$_2$)—OH                  |   |   |   | +   |
| 12  | HIM-CO-Leu-D-Trp-D-Phe(3-COOH)—OH                    |   |   |   | +   |
| 13  | HIM-CO-Leu-D-Trp-D-Phe(4-COOH)—OH                    |   |   |   | +   |
| 14  | HIM-CO-Leu-D-Trp-D-Phe(3-Cl-4-F)—OH                  |   |   |   | + + |
| 15  | HIM-CO-Leu-D-Trp-D-Phe(2,4-Cl)—OH                    |   |   |   | +   |
| 16  | HIM-CO-Leu-D-Trp-D-Phe(2,5-Cl)—OH                    |   |   |   | + + |
| 17  | HIM-CO-Leu-D-Trp-D-Phe(2-CH$_3$-3-Cl)—OH             |   |   |   | +   |
| 18  | HIM-CO-Leu-D-Phe(2-F)-D-Trp-OH                       |   |   |   | +   |
| 19  | HIM-CO-Leu-D-Phe(3-F)-D-Trp-OH                       | + |   |   |     |
| 20  | HIM-CO-Leu-D-Phe(4-F)-D-Trp-OH                       | − |   |   |     |
| 21  | HIM-CO-Leu-D-Phe(4-Br)-D-Trp-OH                      |   |   |   | +   |
| 22  | HIM-CO-Leu-D-Phe(3-NO$_2$)-D-Trp-OH                  |   |   |   | +   |
| 23  | HIM-CO-Leu-D-Phe(4-F-3-Cl)-D-Trp-OH                  |   |   |   | +   |
| 24  | HIM-CO-Leu-D-Phe(3-CO-D-Trp-OH)-D-Trp-OH             |   |   |   | +   |
| 25  | HIM-CO-Leu-D-Phe(4-CO-D-Trp-OH)-D-Trp-OH             |   |   |   | + + |
| 26  | HIM-CO-Leu-D-Phe(2-CH$_3$-3-Cl)-D-Trp-OH             |   | + |   |     |
| 27  | Phenoxy-CO-Pro-D-Trp-D-Phe(2-F)—OH                   |   |   |   | +   |
| 28  | Phenoxy-CO-Pro-D-Trp-D-Phe(3-F)—OH                   |   |   |   | +   |
| 29  | Phenoxy-CO-Pro-D-Trp-D-Phe(4-F)—OH                   |   |   |   | + + |
| 30  | Phenoxy-CO-Pro-D-Trp-D-Phe(2-Cl)—OH                  |   |   |   | +   |
| 31  | Phenoxy-CO-Pro-D-Trp-D-Phe(3-Cl)—OH                  |   |   |   | +   |
| 32  | Phenoxy-CO-Pro-D-Trp-D-Phe(4-Cl)—OH                  | + |   |   |     |
| 33  | Phenoxy-CO-Pro-D-Trp-D-Phe(4-Br)—OH                  |   | + |   |     |
| 34  | Phenoxy-CO-Pro-D-Trp-D-Phe(3-NO$_2$)—OH              |   |   |   | + + |
| 35  | Phenoxy-CO-Pro-D-Trp-D-Phe(4-F-3-Cl)—OH              |   |   |   | +   |
| 36  | Phenoxy-CO-Pro-D-Trp-D-Phe(2,4-Cl)—OH                |   |   |   | +   |
| 37  | Phenoxy-CO-Pro-D-Trp-D-Phe(2,5-Cl)—OH                |   |   |   | +   |
| 38  | Phenoxy-CO-Pro-D-Trp-D-Phe(3-COOH)—OH                |   |   |   | +   |
| 39  | Phenoxy-CO-Pro-D-Trp-D-Phe(4-COOH)—OH                |   |   |   | +   |
| 40  | Phenoxy-CO-Pro-D-Trp-D-Phe(2-CH$_3$-3-Cl)—OH         |   |   |   | +   | o-CPh:

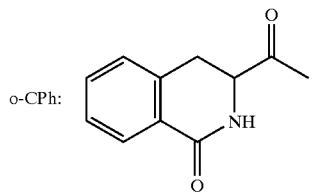

| 41  | o-CPh-D-Trp-D-Phe(2-F)—OH                            |   |   |   | +   |
|     |                                                      |   |   |   | +   |
| 42  | o-CPh-D-Trp-D-Phe(3-F)—OH                            |   |   |   | +   |
| 43  | o-CPh-D-Trp-D-Phe(4-F)—OH                            |   |   |   | +   |
| 44  | o-CPh-D-Trp-D-Phe(2-Cl)—OH                           |   |   |   | +   |
| 45  | o-CPh-D-Trp-D-Phe(3-Cl)—OH                           |   |   |   | +   |
| 46  | o-CPh-D-Trp-D-Phe(4-Cl)—OH                           |   |   |   | +   |
| 47  | o-CPh-D-Trp-D-Phe(4-Br)—OH                           |   |   |   | +   |
| 48  | o-CPh-D-Trp-D-Phe(3-NO$_2$)—OH                       |   |   |   | +   |
| 49  | o-CPh-D-Trp-D-Phe(3-COOH)—OH                         | − |   |   |     |
| 50  | o-CPh-D-Trp-D-Phe(4-COOH)—OH                         | − |   |   |     |
| 51  | o-CPh-D-Trp-D-Phe(2,4-Cl)—OH                         |   |   |   | +   |
| 52  | o-CPh-D-Trp-D-Phe(2,5-Cl)—OH                         | − |   |   |     |
| 53  | o-CPh-D-Trp-D-Phe(2-CH$_3$-Cl)—OH                    |   |   |   | +   |

+ +: strong antagonist affect
+: middle antagonist affect
−: no antagonist affect

What is claimed is:

1. A compound of formula I or a stereoisomer thereof:

RCO-A-B—C—OH    (I)

wherein R is hexamethyleneiminyl or Phenoxy-, or RCO-A is the following structure:

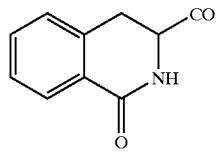

A is Pro, Gly or an aliphatic amino acid;

B is D-Trp, D-Pya, or D-Phe, said D-Phe having a phenyl group, wherein position 2, 3, 4 or 5 of said phenyl group is optionally substituted by one or two members selected from the group consisting of halogen, nitro, carboxyl, and (C1–C4)-alkyl;

C is D-Trp, D-Pya, or D-Phe, said D-Phe having a phenyl group, wherein position 2, 3, 4 or 5 of said phenyl group is optionally substituted by one or two members selected from the group consisting of halogen, nitro, carboxyl, and (C1–C4)-alkyl;

with the proviso that at least one of B and C is D-Trp, and with the proviso that when A is Gly, then R is hexamethyleneiminyl, B is D-Trp and C is D-Trp, and with the proviso that when R is hexamethyleneiminyl or phenoxy, and A is Leu, and B is D-Trp, then C is D-Pya or D-Phe, said D-Phe being substituted at position 2, 3, 4 or 5 of the phenyl group by one or two members selected from the group consisting of halogen, nitro, carboxyl and ($C_1$–$C_4$)-alkyl.

2. The compound of claim 1, wherein said compound is selected from the group consisting of:

HIM-CO—NH—CH2-CO-D-Trp-D-Trp-OH,
HIM-CO-GABA-D-Trp-D-Trp-OH,
HIM-CO—NH—(CH$_2$)$_2$-CO-D-Trp-D-Trp-OH,
HIM-CO-Leu-D-Trp-D-Phe(2-F)—OH,
HIM-CO-Leu-D-Trp-D-Phe(3-F)—OH,
HIM-CO-Leu-D-Trp-D-Phe(4-F)—OH,
HIM-CO-Leu-D-Trp-D-Phe(2-Cl)—OH,
HIM-CO-Leu-D-Trp-D-Phe(3-Cl)—OH,
HIM-CO-Leu-D-Trp-D-Phe(4-Cl)—OH,
HIM-CO-Leu-D-Trp-D-Phe(4-Br)—OH,
HIM-CO-Leu-D-Trp-D-Phe(3-NO$_2$)—OH,
HIM-CO-Leu-D-Trp-D-Phe(3-COOH)—OH,
HIM-CO-Leu-D-Trp-D-Phe(4-COOH)—OH,
HIM-CO-Leu-D-Trp-D-Phe(3-Cl-4-F)—OH,
HIM-CO-Leu-D-Trp-D-Phe(2,4-Cl)—OH,
HIM-CO-Leu-D-Trp-D-Phe(2,5-Cl)—OH,
HIM-CO-Leu-D-Trp-D-Phe(2-CH$_3$-3-Cl)—OH,
HIM-CO-Leu-D-Phe(2-F)-D-Trp-OH,
HIM-CO-Leu-D-Phe(3-F)-D-Trp-OH,
HIM-CO-Leu-D-Phe(4-Br)-D-Trp-OH,
HIM-CO-Leu-D-Phe(3-NO2)-D-Trp-OH,
HIM-CO-Leu-D-Phe(4-F-3-Cl)-D-Trp-OH,
HIM-CO-Leu-D-Phe(3-CO-D-Trp-OH)-D-Trp-OH,
HIM-CO-Leu-D-Phe(4-CO-D-Trp-OH)-D-Trp-OH,
HIM-CO-Leu-D-Phe(2-CH$_3$-3-Cl)-D-Trp-OH,
Phenoxy-CO-Pro-D-Trp-D-Phe(2-F)—OH,
Phenoxy-CO-Pro-D-Trp-D-Phe(3-F)—OH,
Phenoxy-CO-Pro-D-Trp-D-Phe(4-F)—OH,
Phenoxy-CO-Pro-D-Trp-D-Phe(2Cl)—OH,
Phenoxy-CO-Pro-D-Trp-D-Phe(3Cl)—OH
Phenoxy-CO-Pro-D-Trp-D-Phe(4-Cl)—OH,
Phenoxy-CO-Pro-D-Trp-D-Phe(4Br)—OH,
Phenoxy-CO-Pro-D-Trp-D-Phe(3-NO$_2$)—OH,
Phenoxy-CO-Pro-D-Trp-D-Phe(4-F-3-Cl)—OH,
Phenoxy-CO-Pro-D-Trp-D-Phe(2,4-Cl)—OH,
Phenoxy-CO-Pro-D-Trp-D-Phe(2,5-Cl)—OH,
Phenoxy-CO-Pro-D-Trp-D-Phe(3-COOH)—OH,
Phenoxy-CO-Pro-D-Trp-D-Phe(4-COOH)—OH,
Phenoxy-CO-Pro-D-Trp-D-Phe(2-CH$_3$-3-Cl)—OH,
o-CPh-D-Trp-D-Phe(2-F)—OH,
o-CPh-D-Trp-D-Phe(3-F)—OH,
o-CPh-D-Trp-D-Phe(4-F)—OH,
o-CPh-D-Trp-D-Phe(2-Cl)—OH,
o-CPh-D-Trp-D-Phe(3-Cl)—OH,
o-CPh-D-Trp-D-Phe(4-Cl)—OH,
o-CPh-D-Trp-D-Phe(4-Br)—OH,
o-CPh-D-Trp-D-Phe(3-NO$_2$)—OH,
o-CPh-D-Trp-D-Phe(2,4-Cl)—OH, and
o-CPh-D-Trp-D-Phe(2-CH3—Cl)—OH;
wherein o-CPh is

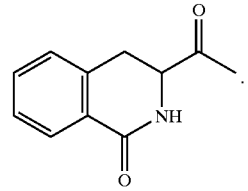

3. The compound of claim 1 or 2, wherein said compound is selected from the group consisting of:

HIM-CO—NH—CH$_2$-CH$_2$-CO-D-Trp-D-Trp-OH,
HIM-CO-GABA-D-Trp-D-Trp-OH,
HIM-CO—NH—(CH$_3$)$_2$-CO-D-Trp-D-Trp-OH,
HIM-CO-Leu-D-Trp-D-Phe(2-F)—OH,
HIM-CO-Leu-D-Trp-D-Phe(3-F)—OH,
HIM-CO-Leu-D-Trp-D-Phe(4-F)—OH,
HIM-CO-Leu-D-Trp-D-Phe(2-Cl)—OH,
HIM-CO-Leu-D-Trp-D-Phe(3-Cl)—OH,
HIM-CO-Leu-D-Trp-D-Phe(4-Cl)—OH,
HIM-CO-Leu-D-Trp-D-Phe(4-Br)—OH,
HIM-CO-Leu-D-Trp-D-Phe(3-NO$_2$)—O,
HIM-CO-Leu-D-Trp-D-Phe(3-COOH)—OH,
HIM-CO-Leu-D-Trp-D-Phe(4-COOH)—OH,
HIM-CO-Leu-D-Trp-D-Phe(3-Cl-4-F)—OH,
HIM-CO-Leu-D-Trp-D-Phe(2,4-Cl)—OH,
HIM-CO-Leu-D-Trp-D-Phe(2,5-Cl)—OH,
HIM-CO-Leu-D-Trp-D-Phe(2-CH$_3$-3-Cl)—OH,
HIM-CO-Leu-D-Phe(2-F)-D-Trp-OH,
HIM-CO-Leu-D-Phe(3-F)-D-Trp-OH,
HIM-CO-Leu-D-Phe(4-Br)-D-Trp-OH,
HIM-CO-Leu-D-Phe(3-NO$_2$)-D-Trp-OH,
HIM-CO-Leu-D-Phe(4-F-3-Cl)-D-Trp-OH,

HIM-CO-Leu-D-Phe(3-CO-D-Trp-OH)-D-Trp-OH,
HIM-CO-Leu-D-Phe(4-CO-D-Trp-OH)-D-Trp-OH, and
HIM-CO-Leu-D-Phe(2-CH$_3$-3-Cl)-D-Trp-OH.

4. A pharmaceutical composition comprising a compound of formula I or a stereoisomer thereof, and a pharmaceutically acceptable carrier or excipient,

RCO-A-B—C—OH (I)

wherein R is hexamethyleneiminyl or Phenoxy-, or R-COA is the following structure:

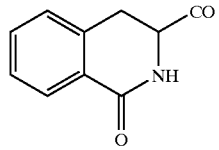

A is Pro, Gly or an aliphatic amino acid;

B is D-Trp, D-Pya, or D-Phe, said D-Phe having a phenyl group, wherein position 2, 3, 4 or 5 of said phenyl group is optionally substituted by one or two members selected from the group consisting of halogen, nitro, carboxyl and (C$_1$–C$_4$)-alkyl;

C is D-Trp, D-Pya, or D-Phe, said D-Phe having a phenyl group, wherein position 2, 3, 4 or 5 of said phenyl group is optionally substituted by one or two members selected from the group consisting of halogen, nitro, carboxyl, and (C$_1$–C$_4$)-alkyl;

with the proviso that at least one of B and C is D-Trp, and with the proviso that when A is Gly, then R is hexamethyleneiminyl, B is D-Trp and C is D-Trp, and with the proviso that when R is hexamethyleneiminyl or phenoxy, and A is Leu, and B is D-Trp, then C is D-Pya or D-Phe, said D-Phe being substituted at, position 2, 3, 4 or 5 of the phenyl group by one or two members selected from the group consisting of halogen, nitro, carboxyl and (C$_1$–C$_4$)-alkyl.

5. The pharmaceutical composition of claim 4, wherein said compound is selected from the group consisting of:

HIM-CO—NH—CH$_2$-CH$_2$-CO-D-Trp-D-Trp-OH,
HIM-CO-GABA-D-Trp-D-Trp-OH,
HIM-CO—NH—(CH$_2$)$_2$-CO-D-Trp-D-Trp-OH,
HIM-CO-Leu-D-Trp-D-Phe(2-F)—OH,
HIM-CO-Leu-D-Trp-D-Phe(3-F)—OH,
HIM-CO-Leu-D-Trp-D-Phe(4-F)—OH,
HIM-CO-Leu-D-Trp-D-Phe(2-Cl)—OH,
HIM-CO-Leu-D-Trp-D-Phe(3-Cl)—OH,
HIM-CO-Leu-D-Trp-D-Phe(4-Cl)—OH,
HIM-CO-Leu-D-Trp-D-Phe(4-Br)—OH,
HIM-CO-Leu-D-Trp-D-Phe(3-NO$_2$)—OH,
HIM-CO-Leu-D-Trp-D-Phe(3-COOH)—OH,
HIM-CO-Leu-D-Trp-D-Phe(4-COOH)—OH,
HIM-CO-Leu-D-Trp-D-Phe(3-Cl-4-F)—OH,
HIM-CO-Leu-D-Trp-D-Phe(2,4-Cl)—OH,
HIM-CO-Leu-D-Trp-D-Phe(2,5-Cl)—OH,
HIM-CO-Leu-D-Trp-D-Phe(2-CH$_3$-3-Cl)—OH,
HIM-CO-Leu-D-Phe(2-F)-D-Trp-OH,
HIM-CO-Leu-D-Phe(3-F)-D-Trp-OH,
HIM-CO-Leu-D-Phe(4-Br)-D-Trp-OH,
HIM-CO-Leu-D-Phe(3-NO$_2$)-D-Trp-OH,
HIM-CO-Leu-D-Phe(4-F-3-Cl)-D-Trp-OH,
HIM-CO-Leu-D-Phe(3-CO-D-Trp-OH)-D-Trp-OH,
HIM-CO-Leu-D-Phe(4-CO-D-Trp-OH)-D-Trp-OH,
HIM-CO-Leu-D-Phe(2-CH$_3$-3-Cl)-D-Trp-OH,
Phenoxy-CO-Pro-D-Trp-D-Phe(2-F)—OH,
Phenoxy-CO-Pro-D-Trp-D-Phe(3-F)—OH,
Phenoxy-CO-Pro-D-Trp-D-Phe(4-F)—OH,
Phenoxy-CO-Pro-D-Trp-D-Phe(2-Cl)—OH,
Phenoxy-CO-Pro-D-Trp-D-Phe(3-Cl)—OH,
Phenoxy-CO-Pro-D-Trp-D-Phe(4-Cl)—OH,
Phenoxy-CO-Pro-D-Trp-D-Phe(4-Br)—OH,
Phenoxy-CO-Pro-D-Trp-D-Phe(3-NO$_2$)—OH,
Phenoxy-CO-Pro-D-Trp-D-Phe(4-F-3-Cl)—OH,
Phenoxy-CO-Pro-D-Trp-D-Phe(2,4-Cl)—OH,
Phenoxy-CO-Pro-D-Trp-D-Phe(2,5-Cl)—OH,
Phenoxy-CO-Pro-D-Trp-D-Phe(3-COOH)—OH,
Phenoxy-CO-Pro-D-Trp-D-Phe(4-COOH)—OH,
Phenoxy-CO-Pro-D-Trp-D-Phe(2-CH$_3$-3-Cl)—OH,
o-CPh-D-Trp-D-Phe(2-F)—OH,
o-CPh-D-Trp-D-Phe(3-F)—OH,
o-CPh-D-Trp-D-Phe(4-F)—OH,
o-CPh-D-Trp-D-Phe(2-Cl)—OH,
o-CPh-D-Trp-D-Phe(3-Cl)—OH,
o-CPh-D-Trp-D-Phe(4-Cl)—OH,
o-CPh-D-Trp-D-Phe(4-Br)—OH,
o-CPh-D-Trp-D-Phe(3-NO$_2$)—OH,
o-CPh-D-Trp-D-Phe(2,4-Cl)—OH, and
o-CPh-D-Trp-D-Phe(2-CH$_3$—Cl)—OH,
wherein o-CPh is

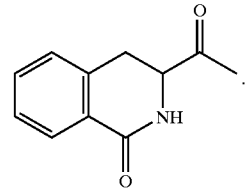

6. The pharmaceutical composition of claim 4 or 5, wherein said compound is selected from the group consisting of:

HIM-CO—NH—CH$_2$-CH$_2$-CO-D-Trp-D-Trp-OH,
HIM-CO-GABA-D-Trp-D-Trp-OH,
HIM-CO—NH—(CH$_3$)$_2$-CO-D-Trp-D-Trp-OH,
HIM-CO-Leu-D-Trp-D-Phe(2-F)—OH,
HIM-CO-Leu-D-Trp-D-Phe(3-F)—OH,
HIM-CO-Leu-D-Trp-D-Phe(4-F)—OH,
HIM-CO-Leu-D-Trp-D-Phe(2-Cl)—OH,
HIM-CO-Leu-D-Trp-D-Phe(3-Cl)—OH,
HIM-CO-Leu-D-Trp-D-Phe(4-Cl)—OH,
HIM-CO-Leu-D-Trp-D-Phe(4-Br)—OH,
HIM-CO-Leu-D-Trp-D-Phe(3-NO$_2$)—OH,
HIM-CO-Leu-D-Trp-D-Phe(3-COOH)—OH,
HIM-CO-Leu-D-Trp-D-Phe(4-COOH)—OH,
HIM-CO-Leu-D-Trp-D-Phe(3-Cl-4-F)—OH,
HIM-CO-Leu-D-Trp-D-Phe(2,4-Cl)—OH,
HIM-CO-Leu-D-Trp-D-Phe(2,5-Cl)—OH,
HIM-CO-Leu-D-Trp-D-Phe(2-CH$_3$-3-Cl)—OH,

HIM-CO-Leu-D-Phe(2-F)-D-Trp-OH,
HIM-CO-Leu-D-Phe(3-F)-D-Trp-OH,
HIM-CO-Leu-D-Phe(4-Br)-D-Trp-OH,
HIM-CO-Leu-D-Phe(3-NO$_2$)-D-Trp-OH,
HIM-CO-Leu-D-Phe(4-F-3-Cl)-D-Trp-OH,
HIM-CO-Leu-D-Phe(3-CO-D-Trp-OH)-D-Trp-OH,
HIM-CO-Leu-D-Phe(4-CO-D-Trp-OH)-D-Trp-OH,
HIM-CO-Leu-D-Phe(2-CH$_3$-3-Cl)-D-Trp-OH.

7. A process for producing the compound of claim 1, comprising:
   A) reacting RCO-A-OH, with B—OP in N,N-dimethylformamide (DMF), dichloromethane (DCM), N-methylmorpholine (NMM) or N,N'-diisopropylcarbodiimide-1-hydroxyl-benzotriazole (DIC-HOBt), wherein P is (C$_1$–C$_4$-alkyl, thereby forming RCO-A-B—OP;
   B) saponifying said RCO-A-B—OP with 1M NaOH,/Methanol and then acidifying with 1M HCl to form RCO-A-B—OH;
   C) reacting said RCO-A-B—OH, with C—OP in DMF, DOM, NMM or DIC-HOBt, to yield RCO-A-B—C—OP, wherein P is (C$_1$–C$_4$)-alkyl;
   D) treating said RCO-A-B—C—OP as recited in step B) for RCO-A-B—OP, to form RCO-A-B—C—OH.

8. The compound of claim 1, wherein said aliphatic amino acid is Leu, β-Ala, γ-aminobutyric acid, or aminoisobutyric acid.

9. The pharmaceutical composition of claim 4, wherein said aliphatic amino acid is Leu, β-Ala, γ-aminobutyric acid, or aminoisobutyric acid.

* * * * *